US012343563B2

(12) United States Patent
MacDonald et al.

(10) Patent No.: US 12,343,563 B2
(45) Date of Patent: Jul. 1, 2025

(54) SYSTEMS AND METHODS FOR PLANNING, CONTROLLING AND/OR DELIVERING RADIOTHERAPY AND RADIOSURGERY USING COMBINED OPTIMIZATION OF DYNAMIC AXES (CODA)

(71) Applicant: DALHOUSIE UNIVERSITY, Halifax (CA)

(72) Inventors: Robert Lee MacDonald, Antigonish (CA); Alasdair Syme, Halifax (CA); Christopher G. Thomas, Halifax (CA); Brian Little, Halifax (CA)

(73) Assignee: Dalhousie University, Halifax (CA)

( * ) Notice: Subject to any disclaimer, the term of this patent is extended or adjusted under 35 U.S.C. 154(b) by 1110 days.

(21) Appl. No.: 17/054,141

(22) PCT Filed: Apr. 18, 2019

(86) PCT No.: PCT/CA2019/050492
§ 371 (c)(1),
(2) Date: Nov. 9, 2020

(87) PCT Pub. No.: WO2019/213743
PCT Pub. Date: Nov. 14, 2019

(65) Prior Publication Data
US 2021/0244970 A1    Aug. 12, 2021

Related U.S. Application Data

(60) Provisional application No. 62/668,114, filed on May 7, 2018.

(51) Int. Cl.
*A61N 5/10* (2006.01)
*G16H 10/60* (2018.01)
(Continued)

(52) U.S. Cl.
CPC ......... *A61N 5/1037* (2013.01); *A61N 5/1045* (2013.01); *A61N 5/1081* (2013.01);
(Continued)

(58) Field of Classification Search
CPC .. A61N 5/1037; A61N 5/1045; A61N 5/1081; A61N 5/1047; A61N 5/1082;
(Continued)

(56) References Cited

U.S. PATENT DOCUMENTS

| 6,546,073 | B1 * | 4/2003 | Lee | A61N 5/1031 378/65 |
| 7,636,419 | B1 * | 12/2009 | Nelson | A61N 5/1048 378/65 |

(Continued)

FOREIGN PATENT DOCUMENTS

| CA | 2568343 A1 | 7/2005 |
| CA | 2796159 A1 | 12/2011 |

(Continued)

OTHER PUBLICATIONS

Matuszak, M.M. et al., "FusionArc optimization: A hybrid volumetric modulated arc therapy (VMAT) and intensity modulated radiation therapy (IMRT) planning strategy", Medical Physics 40(7):071713-1-071713-10, Jul. 2013.

(Continued)

*Primary Examiner* — David A Vanore
(74) *Attorney, Agent, or Firm* — Todd A. Rattray; Oyen Wiggs Green & Mutala LLP

(57) ABSTRACT

Methods and systems for radiation treatment planning and delivery apply a CODA cube. Cost values in the CODA cube may be used in the optimization of couch, collimator, and gantry angles simultaneously. Trajectories generated using the CODA cube show significant benefits when compared to conventional VMAT. A statistically significant sparing to
(Continued)

OAR maximum radiation doses was seen. CODA plans resulted in a reduction to maximum radiation dose in OARs of 20.6% ($p<0.01$), with maximum brainstem radiation dose decreased by 2.63 Gy ($p=0.031$) on average. Mean reduction in total MU was 8.6% ($p=0.156$), and a mean decrease in non-target brain tissue receiving 12 Gy or higher was 3.9% ($p=0.16$), when compared to standard VMAT methods ($n=7$).

21 Claims, 15 Drawing Sheets

(51) Int. Cl.
  *G16H 20/40* (2018.01)
  *G16H 50/70* (2018.01)
(52) U.S. Cl.
  CPC ............ *G16H 10/60* (2018.01); *G16H 20/40* (2018.01); *G16H 50/70* (2018.01)
(58) Field of Classification Search
  CPC ........ A61N 5/103; G16H 10/60; G16H 20/40; G16H 50/70
  See application file for complete search history.

(56) References Cited

U.S. PATENT DOCUMENTS

| | | | |
|---|---|---|---|
| 9,168,392 B1* | 10/2015 | Balakin | A61N 5/1081 |
| 9,421,399 B2* | 8/2016 | Shapiro | A61B 6/4233 |
| 9,498,167 B2* | 11/2016 | Mostafavi | A61N 5/10 |
| RE46,953 E* | 7/2018 | Yu | A61N 5/103 |
| 2013/0142310 A1 | 6/2013 | Fahimian et al. | |
| 2017/0189717 A1 | 7/2017 | MacDonald et al. | |
| 2017/0340900 A1 | 11/2017 | Moore et al. | |
| 2017/0354832 A1* | 12/2017 | Bush | A61N 5/103 |
| 2018/0078785 A1* | 3/2018 | Ollila | A61N 5/1039 |
| 2018/0078789 A1* | 3/2018 | Ollila | A61N 5/1042 |
| 2018/0111005 A1 | 4/2018 | Ranganathan et al. | |
| 2019/0046813 A1 | 2/2019 | Zhou et al. | |
| 2019/0204474 A1* | 7/2019 | Pyrak-Nolte | G01V 1/42 |
| 2020/0101319 A1* | 4/2020 | Haas | A61N 5/1049 |
| 2020/0101320 A1* | 4/2020 | Locke | A61N 5/103 |
| 2020/0101325 A1* | 4/2020 | Ollila | A61N 5/103 |
| 2020/0105394 A1* | 4/2020 | Laaksonen | A61N 5/1064 |
| 2020/0121718 A1* | 4/2020 | Novik | A61K 35/14 |
| 2020/0121957 A1* | 4/2020 | Fishman | A61N 5/1039 |
| 2020/0170598 A1* | 6/2020 | Shea | A61B 8/488 |
| 2020/0206531 A1* | 7/2020 | Locke | A61N 5/1047 |
| 2020/0324144 A1* | 10/2020 | Maltz | A61N 5/1049 |
| 2020/0330795 A1* | 10/2020 | Sawant | A61N 5/1031 |
| 2020/0398079 A1* | 12/2020 | Adelsheim | G16H 50/20 |
| 2021/0090694 A1* | 3/2021 | Colley | G16H 15/00 |
| 2021/0178193 A1* | 6/2021 | Spotts | A61N 5/1044 |
| 2021/0183070 A1* | 6/2021 | Laaksonen | G06T 7/149 |
| 2021/0192279 A1* | 6/2021 | Laaksonen | G16H 30/20 |
| 2021/0192810 A1* | 6/2021 | Paysan | G06T 7/0012 |
| 2021/0299470 A1* | 9/2021 | Nord | G06T 7/0012 |
| 2022/0088410 A1* | 3/2022 | Hibbard | G16H 20/40 |
| 2022/0118282 A1* | 4/2022 | Soukup | A61N 5/1081 |
| 2022/0241614 A1* | 8/2022 | Wu | A61N 5/103 |
| 2022/0296923 A1* | 9/2022 | Peltola | A61N 5/1031 |

FOREIGN PATENT DOCUMENTS

| | | |
|---|---|---|
| CA | 2733415 A1 | 9/2012 |
| CA | 2951048 A1 | 12/2014 |
| EP | 1909904 A1 | 4/2008 |
| EP | 2159725 A1 | 3/2010 |
| WO | 2016008052 A1 | 1/2016 |
| WO | 2016144915 A1 | 9/2016 |
| WO | 2017152286 A1 | 9/2017 |
| WO | 2017218597 A1 | 12/2017 |
| WO | 2018083072 A1 | 5/2018 |
| WO | 2019052925 A1 | 3/2019 |
| WO | 2019090429 A1 | 5/2019 |

OTHER PUBLICATIONS

MacDonald, R.L., Dynamic Trajectory-Based Couch Motion for Improvement of Radiation Therapy Trajectories, M. Sc. thesis, Dalhousie University, submitted Aug. 2014.

Panet-Raymond, V. et al.,"Coplanar versus Noncoplanar Intensity-Modulated Radiation Therapy (IMRT) and Volumetric-Modulated Arc Therapy (VMAT) Treatment Planning for Fronto-Temporal High-Grade Glioma", Journal of Applied Clinical Medical Physics 13(4):44-53, 2012.

Wild, E. et al., "Noncoplanar VMAT for Nasopharyngeal Tumors: Plan Quality versus Treatment Time", Medical Physics 42(5):2157-2168, May 2015.

Langhans, M. et al., "Optimizing Highly Noncoplanar VMAT Trajectories: The NoVo Method", Physics in Medicine and Biology 63(2):025023, Jan. 2018.

MacDonald, R.L. et al., "Dynamic trajectory-based couch motion for improvement of radiation therapy trajectories in cranial SRT", MedPhys. 42(5), May 2015, 2317-2325.

Yang, Y. et al., "Choreographing couch and collimator in volumetric modulated arc therapy", Int. J. Radiation Oncology Biol. Phys. 80(4):1238-1247, 2011.

MacDonald, R.L. et al., "Overlap-guided fixed-patient support positioning optimization for cranial SRT", Med. Phys. 44(1):17-27, Jan. 2017.

"Elements Cranial SRS", Brainlab, accessed Mar. 19, 2018, https://www.brainlab.com/en/radiosurgery-products/brain/cranial-srs/.

"Varian HyperArc: High Definition Radiotherapy—Varian Medical Systems", accessed Mar. 19, 2018, https://www.varian.com/oncology/solutions/hyperarc.

Marks, L.B. et al., "The Use of Normal Tissue Complication Probability (NTCP) Models in the Clinic", Int J Radiat Oncol Biol Phys. 76:S10-S19, Mar. 2010.

Hall, E.J. et al., "Table 19.2, chapter 19: clinical response of normal tissues", In: Radiobiology for the Radiologist, Philadelphia, PA, Lippincott Williams & Wilkins, 2006: 303-327.

MacDonald, R.L. et al., "Dynamic collimator trajectory algorithm for multiple metastases dynamic conformal arc treatment planning", Med. Phys. 45(1):5-17, Jan. 2018.

Varian Medical Systems Eclipse Algorithms Reference Guide, Apr. 2010.

Andrews, D.W. et al., "Whole brain radiation therapy with or without stereotactic radiosurgery boost for patients with one to three brain metastases: phase III results of the RTOG 9508 randomised trial", The Lancet, vol. 363, Issue 9422, 1665-1672, May 2004.

Clark, G.M. et al., "Plan quality and treatment planning technique for single isocenter cranial radiosurgery with volumetric modulated arc therapy", Practical Radiation Oncology 2:306-313, 2012.

Van'T Riet, A. et al., "A conformation number to quantify the degree of conformality in brachytherapy and external beam irradiation: application to the prostate", Int. J. Radiation Oncology Biol. Phys. 37(3):731-736, 1997.

Kanungo, T. et al., "An Efficient k-Means Clustering Algorithm: Analysis and Implementation", IEEE Transactions on Pattern Analysis and Machine Intelligence 24(7):881-892, Jul. 2002.

Smyth, G. et al., "Recent Developments in Non-Coplanar Radiotherapy", The British Journal of Radiology 92, No. 1097, May 2019.

* cited by examiner

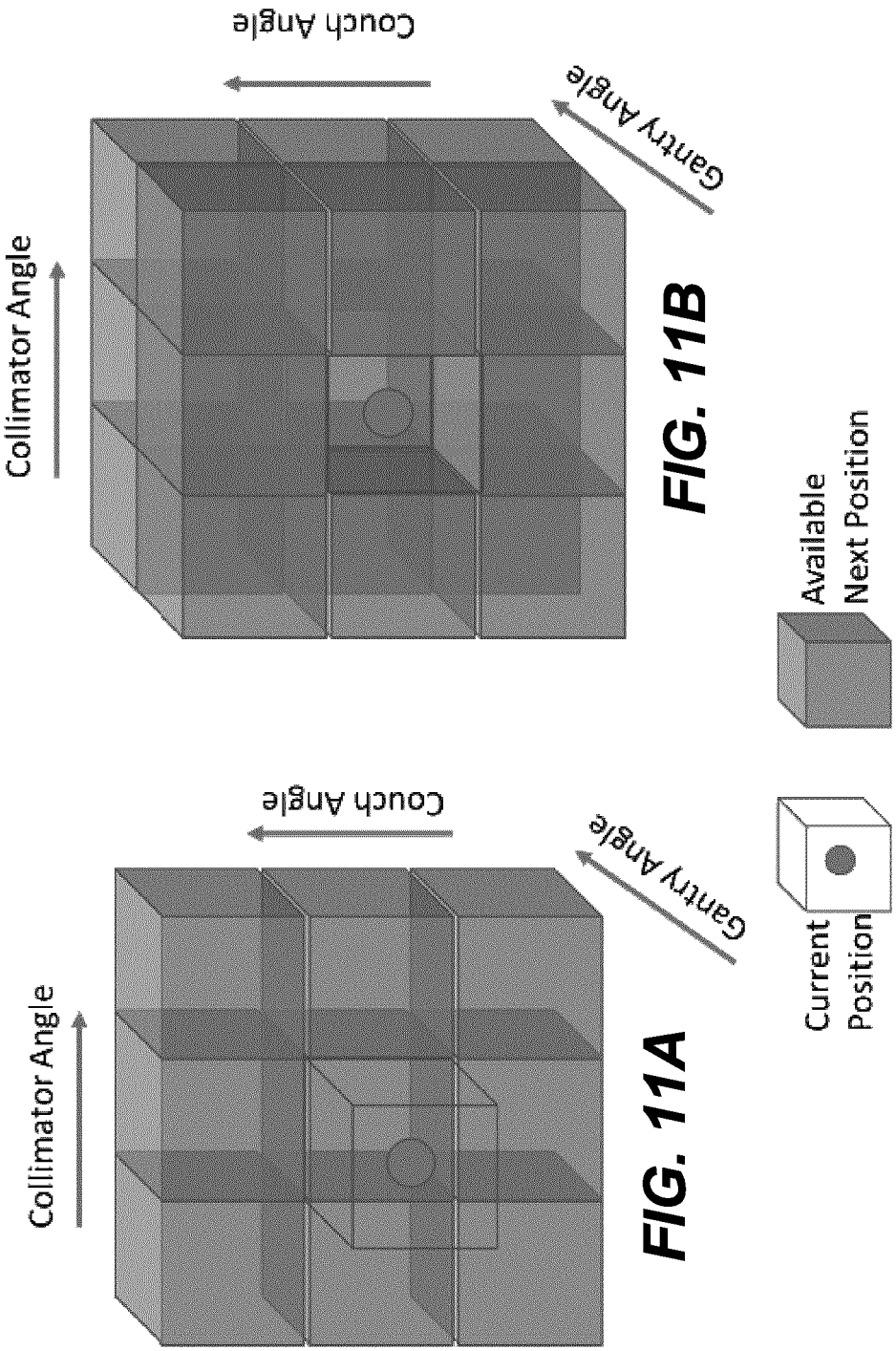
FIG. 11A
FIG. 11B

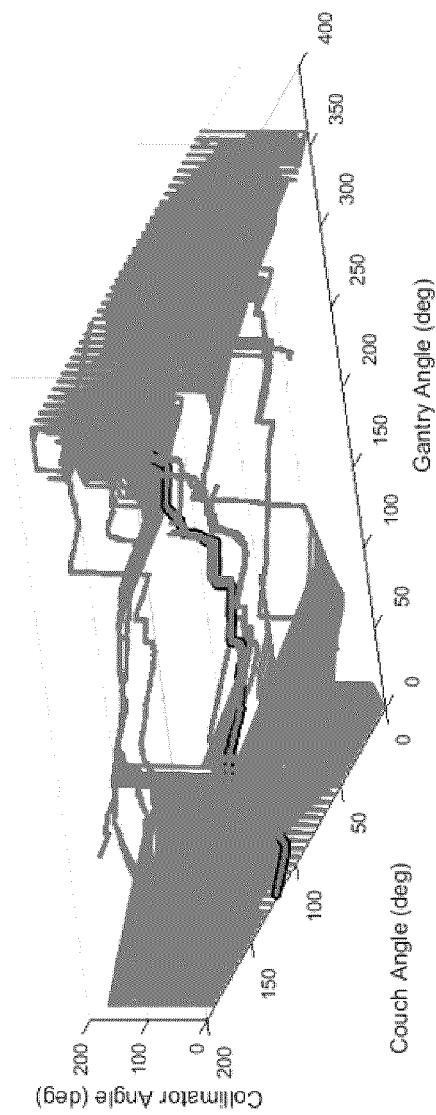
FIG. 12A
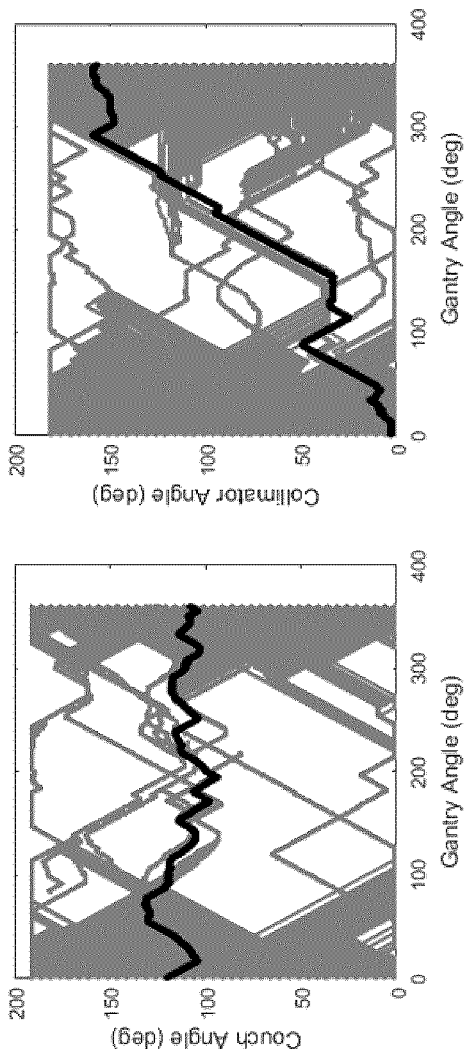
FIG. 12B
FIG. 12C

SYSTEMS AND METHODS FOR PLANNING, CONTROLLING AND/OR DELIVERING RADIOTHERAPY AND RADIOSURGERY USING COMBINED OPTIMIZATION OF DYNAMIC AXES (CODA)

CROSS-REFERENCE TO RELATED APPLICATION

This application claims priority from U.S. Application No. 62/668,114 filed 7 May 2018. For purposes of the United States, this application claims the benefit under 35 U.S.C. § 119 of U.S. Application No. 62/668,114 filed 7 May 2018 and entitled SYSTEMS AND METHODS FOR PLANNING, CONTROLLING AND/OR DELIVERING RADIOTHERAPY AND RADIOSURGERY USING COMBINED OPTIMIZATION OF DYNAMIC AXES (CODA), which is hereby incorporated herein by reference for all purposes.

FIELD

The present disclosure relates to radiotherapy devices and methods related to planning and/or delivering radiotherapy. More particularly, the present disclosure relates to the use and/or control of radiotherapy devices to deliver prescribed radiation doses to defined volumes. Some embodiments provide systems and methods useful in planning and/or controlling delivery of radiotherapy.

BACKGROUND

Radiotherapy involves delivering radiation to a subject. A non-limiting example application of radiotherapy is cancer treatment. Radiotherapy is widely used for treating tumors in the brain, for example. The radiation used for radiotherapy may comprise photon beams (e.g. x-rays) or particle beams (e.g. proton beams). Radiation for treatment of cancers and other conditions may, for example, be generated by a linear accelerator.

Ideally a radiotherapy treatment would deliver a prescribed radiation dose to a target volume (e.g. a brain tumor) while delivering no radiation outside of the target volume (e.g. to brain tissue and/or other tissue that surrounds the brain tumor). In this ideal case, all non-targeted tissues would receive no radiation exposure. This is not possible, in general, because the radiation beams used for radiotherapy must typically pass through overlying tissues to reach a target volume. The radiation beams deliver radiation dose to these overlying tissues as they pass through. Further, the radiation beams are not extinguished in the target volume. The radiation beams pass through the target volume and deliver radiation dose to tissues on the side of the target volume away from the radiation source. Scattering of radiation from a radiation beam is another mechanism by which radiation dose is delivered outside of a target volume.

Some non-target tissues may be more sensitive to radiation exposure and/or more critical than others. Such non-targeted tissue may be called an organ-at-risk (OAR). It can be desirable to minimize radiation dose delivered to OARs. For example, in delivering radiation to locations within a patient's brain, it is generally desirable to minimize radiation dose delivered to the patient's optic nerves and brain-stem, each of which may be considered to be an OAR in at least some applications.

Although it is impossible to avoid delivering radiation dose to tissues outside of a target volume, the amount of radiation dose delivered outside of the target volume and the way in which that radiation dose is distributed in non-target tissues can be affected very significantly by how the radiation is delivered to the target volume. For example, a target volume may be irradiated by radiation beams incident from many directions which collectively deliver a prescribed radiation dose to the target volume. This may result in relatively low radiation doses to non-target tissue outside of the target volume while achieving a distribution of radiation dose within the target volume that more accurately matches a prescription (for example, the prescription may call for a specified uniform radiation dose within the target volume).

The field of radiation treatment planning has been and remains the subject of a large amount of active research. This research has yielded various approaches to planning and delivering radiotherapy.

Arc therapies are one example class of radiotherapies. Arc therapies involve moving a radiation source along a treatment trajectory (typically an arc) extending at least part way around a patient. Radiation doses are delivered to a target volume from locations on the trajectory. In some arc therapies, radiation is delivered continuously or substantially continuously as the radiation source is moved along the trajectory. By irradiating target volumes from a variety of angles, arc therapies aim to achieve the prescription radiation doses assigned to planning target volumes while limiting the radiation exposure to non-target tissues (e.g. healthy normal tissue, sensitive structures, OARs, etc.).

Some radiotherapy devices provide multiple degrees of freedom for adjusting relative position of a radiation source and target tissue. For example, some radiotherapy devices allow for rotation of a patient support couch. Such devices are described, for example, in MacDonald, *Dynamic Trajectory-Based Couch Motion for Improvement of Radiation Therapy Trajectories*, M. Sc. thesis Dalhousie University, submitted August 2014 and PCT patent publication No. WO2016008052 entitled METHOD AND SYSTEM FOR CANCER TREATMENT WITH RADIATION both of which are hereby incorporated herein by reference for all purposes.

Conformal arc therapies involve shaping a radiation beam (for example, a cone beam), such that a cross-section of the beam is shaped to conform to the projection of the target volume in the beam's-eye-view (i.e. a view taken along a central axis of the radiation beam, abbreviated as BEV). Beam shaping is typically achieved by passing the beam through a beam shaper having an aperture that can be adjusted to conform at least roughly to the shape of the projection of the target volume. Deviations between the shape of the aperture and the boundary of the projection of the target volume and leakage of radiation through parts of the beam shaper that are intended to block radiation are another source of radiation dose to non-target tissues and/or deviations from prescribed radiation dose within the target volume.

One type of beam shaper is a multi-leaf collimator (MLC). Some MLCs have two sets of leaves that can be advanced or retracted from either side of an opening to define a desired aperture. Some MLCs such as the Varian Halcyon™ MLC have four sets of leaves. In some treatment modalities, positions of the leaves of a MLC are adjusted dynamically to change the shaping of a radiation beam as the beam source is moved along a trajectory.

For target volumes having certain shapes, the degree to which a radiation beam can be shaped by the leaves of a MLC to match the shape of the projection of the target volume can depend on the relative orientations of the target volume and the MLC leaves. Some arc therapy modalities that apply a MLC allow the MLC to be rotated to optimize beam shaping to match the projection of a target volume for different points along the trajectory. Arc therapies include, but are not limited to, dynamic conformal arc therapy and volumetric modulated arc therapy (VMAT).

Another type of arc therapy is intensity modulated arc therapy (IMAT). IMAT involves modulating the intensity of a radiation field. The intensity modulated radiation field can be shaped (for example, using a MLC) to improve conformation of a delivered radiation dose distribution to a prescribed radiation dose distribution.

In general, beam shapers, including MLCs, cannot completely block parts of a radiation beam. Radiation that leaks through the beam shaper outside of the aperture (e.g. through MLC leaves, through the joints between MLC leaves, etc.) can deliver non-negligible radiation doses to non-targeted tissues.

A wide range of approaches to radiation treatment planning have been discussed in the academic and patent literature. Some examples are described in the following publications:

1. Panet-Raymond, Valerie, Will Ansbacher, Sergei Zavgorodni, Bill Bendorffe, Alan Nichol, Pauline T. Truong, Wayne Beckham, and Maria Vlachaki. "Coplanar versus Noncoplanar Intensity-Modulated Radiation Therapy (IMRT) and Volumetric-Modulated Arc Therapy (VMAT) Treatment Planning for Fronto-Temporal High-Grade Glioma." Journal of Applied Clinical Medical Physics 13, no. 4 (Jul. 5, 2012): 3826.
2. Wild, Esther, Mark Bangert, Simeon Nill, and Uwe Oelfke. "Noncoplanar VMAT for Nasopharyngeal Tumors: Plan Quality versus Treatment Time." Medical Physics 42, no. 5 (May 2015): 2157-68.
3. Langhans, Marco, Jan Unkelbach, Thomas Bortfeld, and David Craft. "Optimizing Highly Noncoplanar VMAT Trajectories: The NoVo Method." Physics in Medicine and Biology 63, no. 2 (Jan. 16, 2018).
4. MacDonald, R. L., Thomas C G. Dynamic trajectory-based couch motion for improvement of radiation therapy trajectories in cranial SRT. MedPhys. 2015; 42:2317-2325.
5. Yang Y, Zhang P, Happersett L, et al. Choreographing couch and collimator in volumetric modulated arc therapy. Int J Radiati Oncol BiolPhys. 2011; 80:1238-1247.
6. MacDonald, R. L., Robar, J. L. and Thomas, C. G. (2017), Overlap-guided fixed-patient support positioning optimization for cranial SRT. Med. Phys., 44:17-27. doi: 10.1002/mp.12008.
7. "Elements Cranial SRS." Brainlab. Accessed Mar. 19, 2018. https://www.brainlab.com/en/radiosurgery-products/brain/cranial-srs/.
8. "Varian HyperArc: High Definition Radiotherapy-Varian Medical Systems". Accessed Mar. 19, 2018. https://www-.varian.com/oncology/solutions/hyperarc.
9. Marks L B, Yorke E D, Jackson A, et al. Use of normal tissue complication probability models in the clinic. Int J Radiat Oncol Biol Phys. 2010; 76: S10-S19.
10. Hall E J, A J Giaccia. Table 19.2, chapter 19: clinical response of normal tissues. In: Radiobiology for the Radiologist. Philadelphia, P A: Lippincott Williams & Wilkins; 2006:303-327.
11. MacDonald, R. L., Thomas, C. G. and Syme, A. (2018), Dynamic collimator trajectory algorithm for multiple metastases dynamic conformal arc treatment planning. Med. Phys., 45:5-17. doi: 10.1002/mp.12648.
12. Varian Medical Systems Eclipse Algorithms Reference Guide; April 2010.
13. Whole brain radiation therapy with or without stereotactic radiosurgery boost for patients with one to three brain metastases: phase III results of the RTOG 9508 randomised trial, Andrews, David W et al. The Lancet, Volume 363, Issue 9422, 1665-1672.
14. Clark G M, Popple R A, Prendergast B M, et al. Plan quality and treatment planning technique for single isocenter cranial radiosurgery with volumetric modulated arc therapy. Pract Radiat Oncol. 2012; 2:306-313.
15. Van't Riet A, Mak A C, Moerland M A, Elders L H, derVan Zee W. A conformation number to quantify the degree of conformality in brachytherapy and external beam irradiation: application to the prostate. Int J Radiat Oncol Biol Phys. 1997; 37:731-736.
16. WO2017218597A1.

Commercially available radiation treatment planning systems implement some of these approaches. While some of these approaches can yield radiation dose distributions that are close to the best that can be achieved for certain geometries of target volumes, there remains a need for practical approaches that can yield better radiation dose distributions for other target volume geometries. There is also a need for practical approaches that can deliver prescribed radiation doses efficiently (e.g. quickly and/or with a relatively small total radiation output of the radiation delivery device).

SUMMARY

This invention has a number of aspects. These include, without limitation:
  radiation treatment planning systems;
  methods for radiation treatment planning;
  methods and apparatus for defining patient-specific trajectories for radiotherapy;
  methods for delivery of radiotherapy;
  control systems for radiotherapy devices; and
  radiotherapy systems.

One aspect of the invention provides a method for generating a radiation treatment plan for delivery by a radiotherapy device comprising a gantry rotatable through a range of gantry angles, a patient support couch rotatable through a range of couch angles, and a multi-leaf collimator rotatable through a range of collimator angles. The method may comprise generating a data cube comprising a three-dimensional array of voxels wherein each of the voxels corresponds to a corresponding gantry angle within the range of gantry angles, a corresponding couch angle within the range of couch angles and a corresponding collimator angle within the range of collimator angles. The method may include: computing a value of a cost function based on patient data and machine data for each of the voxels, the patient data defining one or more target regions and one or more regions corresponding to organs at risk (OARs); and storing the resulting values of the cost function in locations in a data store associated with the corresponding voxels. The method may also comprise processing the values in the data cube to determine plural candidate arcs that collectively span at least a predetermined portion of the range of gantry angles wherein the candidate arcs each pass from a corresponding first endpoint voxel through contiguous ones of the voxels to a corresponding second endpoint voxel and for which a sum of the cost function values over the candidate trajectory is minimized. The method may also comprise generating an optimized radiation delivery plan for delivery of prescribed radiation dose to the one or more target regions using a plurality of the candidate arcs by inverse optimization.

In some embodiments determining the candidate arcs comprises, for planes each corresponding to a fixed collimator angle, identifying arcs lying in the plane that piecewise span the predetermined portion of the range of gantry angles while minimizing a sum of the values of the voxels lying in the arcs.

In some embodiments the predetermined portion of the range of gantry angles is the range of gantry angles.

In some embodiments the method comprises constraining the candidate arcs to have at least a minimum arc length.

In some embodiments determining the candidate arcs comprises constraining the number of candidate arcs in each of the planes to not exceed a maximum number of candidate arcs per plane.

In some embodiments the method comprises associating the candidate arcs to a plurality of clusters, selecting one of the candidate arcs for each of the plurality of clusters and generating the optimized radiation delivery plan using the selected candidate arcs.

In some embodiments associating the candidate arcs to the plurality of clusters comprises performing a k-means clustering algorithm.

In some embodiments selecting one of the candidate arcs for each of the plurality of clusters comprises selecting a longest one of the candidate arcs associated to the cluster.

In some embodiments the cost function comprises a combination of a first cost associated with exposure of the OARs to radiation and a second cost associated with exposure of non-target tissues to radiation.

In some embodiments the cost function combines outputs of a plurality of objective functions.

In some embodiments the method comprises normalizing the outputs of each of the plurality of objective functions before combining the outputs of the objective functions.

In some embodiments combining the outputs of the objective functions comprises determining a mean of the outputs of the plural objective functions.

In some embodiments the plurality of objective functions comprises a 4π objective function.

In some embodiments the plurality of objective functions comprises a whitespace objective function.

In some embodiments processing the values in the data cube comprises applying a Bellman-Ford algorithm.

In some embodiments each of the candidate arcs comprises an arc along which gantry angle changes and couch angle is fixed.

In some embodiments the inverse optimization optimizes collimator leaf configurations for the multi-leaf collimator along the plurality of the candidate arcs.

In some embodiments the inverse optimization comprises optimizing dose rate along the plurality of the candidate arcs.

Another aspect of the invention provides a method for generating a radiation treatment plan for delivery by a radiotherapy device having plural degrees of freedom. The method may comprise generating a data structure representing a cost space having three or more dimensions by: computing a value of a cost function based on patient data and machine data for each of a plurality of coordinate points wherein each of the coordinate points corresponds to a set of control point values, each of the sets of control point values comprising, for each of the plural degrees of freedom, one of a plurality of control point values that indicate positions of the radiotherapy device in the corresponding degree of freedom; and storing the resulting values of the cost function in locations in a data store associated with the corresponding coordinate points. In some embodiments the method may also comprise processing the data in the data structure to determine plural candidate trajectories that each pass successively through neighboring ones of the coordinate points and for which a sum of the cost function values over the candidate trajectory is smaller than for other possible trajectories. The method may also comprise generating an optimized radiation delivery plan using a plurality of the candidate trajectories.

In some embodiments the method comprises selecting the plurality of the candidate trajectories using a clustering algorithm.

In some embodiments the clustering algorithm comprises a k-means clustering algorithm.

In some embodiments selecting the plurality of the candidate trajectories comprises selecting the longest trajectory from each of a plurality of clusters determined by the clustering algorithm.

In some embodiments the plural degrees of freedom include a gantry angle, a couch angle and a collimator rotation angle.

In some embodiments the candidate trajectories lie in planes in which one direction in the planes corresponds to gantry angle and another direction in the planes corresponds to couch angle.

In some embodiments the method comprises separately identifying candidate trajectories in each of plural ones of the planes.

In some embodiments the method comprises, for each of the planes finding a set of not more than $N_{max}$ trajectories that piecewise span the full range of possible gantry angles with a minimum total cost.

In some embodiments the method comprises constraining the trajectories to satisfy a trajectory length criterion requiring each trajectory to have at least a minimum length.

In some embodiments each of the trajectories comprises an arc along which gantry angle changes and couch angle is fixed.

In some embodiments processing the data in the data structure to determine the candidate trajectories comprises applying a Bellman-Ford algorithm.

In some embodiments generating the optimized radiation treatment plan comprises performing inverse optimization.

In some embodiments the radiotherapy device comprises a multi-leaf collimator and the inverse optimization optimizes collimator leaf configuration for the multi-leaf collimator along the treatment trajectories.

In some embodiments the inverse optimization comprises optimizing radiation dose rate along the treatment trajectories.

In some embodiments the trajectories involve motions in one of the degrees of freedom only.

In some embodiments the cost function comprises plural objective functions.

In some embodiments the method comprises determining a mean of the values of the plural objective functions.

In some embodiments the objective functions comprise a 4π objective function and a whitespace objective function.

In some embodiments the cost function penalizes dose to organs at risk (OARs) identified in the patient data.

In some embodiments the cost function penalizes dose to non-target tissues.

In some embodiments the data structure comprises a cube having dimensions that span the entire range of the degrees of freedom.

Another aspect of the invention provides a method for establishing trajectories for delivering radiation treatment by a radiotherapy device having plural degrees of freedom. The method may comprise generating a data structure representing a cost space having three or more dimensions by: computing a value of a cost function based on patient data and machine data for each of a plurality of coordinate points wherein each of the coordinate points corresponds to a set of control point values, each of the sets of control point values comprising, for each of the plural degrees of freedom, one of a plurality of control point values that indicate positions of the radiotherapy device in the corresponding degree of freedom; and storing the resulting values of the cost function in locations in a data store associated with the corresponding coordinate points. The method may also comprise processing the data in the data structure to determine plural candidate trajectories that each pass successively through neighboring ones of the coordinate points and for which a sum of the cost function values over the candidate trajectory is smaller than for other possible trajectories. The method may also comprise selecting the trajectories from the candidate trajectories.

Another aspect of the invention provides a method for establishing trajectories for delivering radiation treatment by a radiotherapy device comprising a gantry rotatable through a range of gantry angles, a patient support couch rotatable through a range of couch angles, and a multi-leaf collimator rotatable through a range of collimator angles. The method may comprise generating a data cube comprising a three-dimensional array of voxels wherein each of the voxels corresponds to a corresponding gantry angle within the range of gantry angles, a corresponding couch angle within the range of couch angles and a corresponding collimator angle within the range of collimator angles by: computing a value of a cost function based on patient data and machine data for each of the voxels, the patient data defining one or more target regions and one or more regions corresponding to organs at risk (OARs); and storing the resulting values of the cost function in locations in a data store associated with the corresponding voxels. The method may also comprise processing the values in the data cube to determine plural candidate arcs that collectively span at least a predetermined portion of the range of gantry angles wherein the candidate arcs each pass from a corresponding first endpoint voxel through contiguous ones of the voxels to a corresponding second endpoint voxel and for which a sum of the cost function values over the candidate trajectory is minimized. The method may also comprise selecting the trajectories from the candidate arcs.

Radiation treatment plans may comprise sets of instructions executable by a control system of a radiotherapy system. Such instructions may be stored in a data store for future use or medical records, applied to a simulation to evaluate the effectiveness of the radiation treatment plan and/or applied to control a radiotherapy system to configure the radiotherapy system for delivery of radiation according to the radiation treatment plan.

Another aspect of the invention provides methods for radiotherapy which involve controlling a radiotherapy system according to a radiation treatment plan that has been generated as described herein to deliver radiation to a target.

Another aspect of the invention provides an apparatus for generating a trajectory for delivery of radiation by a radiotherapy device comprising a gantry rotatable through a range of gantry angles, a patient support couch rotatable through a range of couch angles, and a multi-leaf collimator rotatable through a range of collimator angles. The apparatus may comprise a data cube comprising a three-dimensional array of voxels wherein each of the voxels corresponds to a corresponding gantry angle within the range of gantry angles, a corresponding couch angle within the range of couch angles and a corresponding collimator angle within the range of collimator angles. The data cube may comprise, in a data storage location corresponding to each of the voxels a value of a cost function based on patient data and machine data for the voxel, the patient data defining one or more target regions and one or more regions corresponding to organs at risk (OARs). The apparatus may also comprise a processor configured to process the values in the data cube to determine a set of plural candidate trajectories that collectively span at least a predetermined portion of the range of gantry angles wherein the candidate trajectories each pass from a corresponding first endpoint voxel through contiguous ones of the voxels to a corresponding second endpoint voxel and for which a sum of the cost function values over the set of candidate trajectories is minimized.

In some embodiments the processor is configured to determine the candidate arcs by, for planes each corresponding to a fixed collimator angle, identifying arcs lying in the plane that piecewise span the predetermined portion of the range of gantry angles while minimizing a sum of the values of the voxels lying in the arcs.

In some embodiments the predetermined portion of the range of gantry angles is the full range of gantry angles.

In some embodiments the candidate arcs are constrained to have at least a minimum arc length.

In some embodiments the processor is configured to constrain the number of candidate arcs in each of the planes to not exceed a maximum number of candidate arcs per plane.

In some embodiments the processor is configured to cluster the candidate arcs into a plurality of clusters, and to select one of the candidate arcs for each of the plurality of clusters.

In some embodiments the processor is configured to associate the candidate arcs to the plurality of clusters by performing a k-means clustering algorithm.

In some embodiments the processor is configured to select a longest one of the candidate arcs associated to each of the plurality of clusters.

In some embodiments the cost function comprises a combination of a first cost associated with exposure of the OARs to radiation and a second cost associated with exposure of non-target tissues to radiation.

In some embodiments the cost function combines outputs of a plurality of objective functions.

In some embodiments the outputs of each of the plurality of objective functions are normalized.

In some embodiments the processor is configured to combine the outputs of the objective functions by determining a mean of the outputs of the plural objective functions.

In some embodiments the plurality of objective functions comprises a $4\pi$ objective function.

In some embodiments the plurality of objective functions comprises a whitespace objective function.

In some embodiments processing the values in the data cube comprises applying a Bellman-Ford algorithm.

In some embodiments each of the candidate arcs comprises an arc along which gantry angle changes and couch angle is fixed.

In some embodiments the inverse optimization optimizes collimator leaf configurations for the multi-leaf collimator along the plurality of the candidate arcs.

In some embodiments the inverse optimization comprises optimizing dose rate along the plurality of the candidate arcs.

Another aspect of the invention provides an apparatus for generating a radiation treatment plan for delivery by a radiotherapy device having plural degrees of freedom. The apparatus may comprise a data structure representing a cost space having three or more dimensions. The data structure may be generated by: computing a value of a cost function based on patient data and machine data for each of a plurality of coordinate points wherein each of the coordinate points corresponds to a set of control point values, each of the sets of control point values comprising, for each of the plural degrees of freedom, one of a plurality of control point values that indicate positions of the radiotherapy device in the corresponding degree of freedom; and storing the resulting values of the cost function in storage locations associated with the corresponding coordinate points. The apparatus may also comprise a data store for storing the resulting values of the cost function. The apparatus may also comprise a processor. The processor may be configured to: process the data in the data structure to determine plural candidate trajectories that each pass successively through neighboring ones of the coordinate points and for which a sum of the cost function values over the candidate trajectory is smaller than for other possible trajectories; and generate an optimized radiation delivery plan using a plurality of the candidate trajectories.

In some embodiments the plurality of the candidate trajectories are selected using a clustering algorithm.

In some embodiments the clustering algorithm comprises a k-means clustering algorithm.

In some embodiments selecting the plurality of the candidate trajectories comprises selecting the longest trajectory from each of a plurality of clusters determined by the clustering algorithm.

In some embodiments the plural degrees of freedom include a gantry angle, a couch angle and a collimator rotation angle.

In some embodiments the candidate trajectories lie in planes in which one direction in the planes corresponds to gantry angle and another direction in the planes corresponds to couch angle.

In some embodiments candidate trajectories in each of plural ones of the planes are separately identified.

In some embodiments, for each of the planes, a set of not more than $N_{max}$ trajectories that piecewise span the full range of possible gantry angles with a minimum total cost is found.

In some embodiments the trajectories to satisfy a trajectory length criterion are constrained requiring each trajectory to have at least a minimum length.

In some embodiments each of the trajectories comprises an arc along which gantry angle changes and couch angle is fixed.

In some embodiments processing the data in the data structure to determine the candidate trajectories comprises applying a Bellman-Ford algorithm.

In some embodiments generating the optimized radiation treatment plan comprises performing inverse optimization.

In some embodiments the radiotherapy device comprises a multi-leaf collimator and the inverse optimization optimizes collimator leaf configuration for the multi-leaf collimator along the treatment trajectories.

In some embodiments the inverse optimization comprises optimizing radiation dose rate along the treatment trajectories.

In some embodiments the trajectories involve motions in one of the degrees of freedom only.

In some embodiments the cost function comprises plural objective functions.

In some embodiments a mean of the values of the plural objective functions is determined.

In some embodiments the objective functions comprise a $4\pi$ objective function and a whitespace objective function.

In some embodiments the cost function penalizes dose to organs at risk (OARs) identified in the patient data.

In some embodiments the cost function penalizes dose to non-target tissues.

In some embodiments the data structure comprises a cube having dimensions that span the entire range of the degrees of freedom.

Another aspect of the invention provides an apparatus for establishing trajectories for delivering radiation treatment by a radiotherapy device having plural degrees of freedom. The apparatus may comprise a data structure representing a cost space having three or more dimensions. The data structure may be generated by: computing a value of a cost function based on patient data and machine data for each of a plurality of coordinate points wherein each of the coordinate points corresponds to a set of control point values, each of the sets of control point values comprising, for each of the plural degrees of freedom, one of a plurality of control point values that indicate positions of the radiotherapy device in the corresponding degree of freedom; and storing the resulting values of the cost function in storage locations associated with the corresponding coordinate points. The apparatus may also comprise a data store for storing the resulting values of the cost function. The apparatus may also comprise a processor. The processor may be configured to: process the data in the data structure to determine plural candidate trajectories that each pass successively through neighboring ones of the coordinate points and for which a sum of the cost function values over the candidate trajectory is smaller than for other possible trajectories; and select the trajectories from the candidate trajectories.

Another aspect of the invention provides an apparatus for establishing trajectories for delivering radiation treatment by a radiotherapy device comprising a gantry rotatable through a range of gantry angles, a patient support couch rotatable through a range of couch angles, and a multi-leaf collimator rotatable through a range of collimator angles. The apparatus may comprise a data cube comprising a three-dimensional array of voxels wherein each of the voxels corresponds to a corresponding gantry angle within the range of gantry angles, a corresponding couch angle within the range of couch angles and a corresponding collimator angle within the range of collimator angles. The data cube may comprise a data structure storing values of a cost function based on patient data and machine data for each of the voxels, the patient data defining one or more target regions and one or more regions corresponding to organs at risk (OARs). The apparatus may also comprise a processor configured to: process the values in the data cube to determine a set of plural candidate arcs that collectively span at least a predetermined portion of the range of gantry angles wherein the candidate arcs each pass from a corresponding first endpoint voxel through contiguous ones of the voxels to a corresponding second endpoint voxel and for which a sum of the cost function values over the set of candidate trajectories is minimized; and select the trajectories from the candidate arcs.

Another aspect of the invention provides an apparatus for generating a radiation treatment plan for delivery by a radiotherapy device comprising a gantry rotatable through a range of gantry angles, a patient support couch rotatable through a range of couch angles, and a multi-leaf collimator rotatable through a range of collimator angles. The apparatus may comprise a cost function computation module, the cost function computation module computing a value of a cost function based on patient data and machine data, the patient data defining one or more target regions and one or more regions corresponding to organs at risk (OARs). The apparatus may also comprise a data cube generation module, the data cube generation module generating a data cube comprising a three-dimensional array of voxels wherein each of the voxels corresponds to a corresponding gantry angle within the range of gantry angles, a corresponding couch angle within the range of couch angles and a corresponding collimator angle within the range of collimator angles, the data cube generation module storing the value of the cost function for each of the voxels in locations in a data store associated with the corresponding voxels. The apparatus may also comprise a data cube processing module, the data cube processing module processing the values in the data cube to determine a set of plural candidate trajectories that collectively span at least a predetermined portion of the range of gantry angles wherein the candidate trajectories each pass from a corresponding first endpoint voxel through contiguous ones of the voxels to a corresponding second endpoint voxel and for which a sum of the cost function values over the set of candidate trajectories is minimized. The apparatus may also comprise an inverse planning module, the inverse planning module generating by inverse optimization an optimized radiation delivery plan for delivery of prescribed radiation dose to the one or more target regions using one or more of the candidate trajectories, the patient data and the machine data.

In some embodiments the cost function combination module combines outputs of a plurality of objective functions.

In some embodiments the outputs of each of the plurality of objective functions is normalized before combining the outputs of the objective functions.

In some embodiments combining the outputs of the objective functions comprises determining a mean of the outputs of the plural objective functions.

In some embodiments the plurality of objective functions comprises a 4π objective function.

In some embodiments the plurality of objective functions comprise a whitespace objective function.

Further aspects and example embodiments are illustrated in the accompanying drawings and/or described in the following description.

BRIEF DESCRIPTION OF THE DRAWINGS

The accompanying drawings illustrate non-limiting example embodiments of the invention.

FIGS. 3A, 3B and 3C are respectively a single plane of a 4π objective function map for all target volumes and organs-at-risk included in an optimization; a couch-gantry plane of a whitespace cube taken for a single collimator angle; and a pixel-wise mean of the planes shown in FIGS. 3A and 3B.

FIG. 7A shows total plan monitor units. FIG. 7B shows an example volume of brain tissue receiving 12 Gy or more. FIG. 7C shows inverse van Riet conformity index (all targets, n=24). FIG. 7D shows maximum radiation dose to a brainstem in Gy. All illustrated error bars show standard deviation.

FIGS. 11A and 11B schematically depict a 3D bi-direction gradient trajectory offering available next trajectory positions from a current position.

FIG. 12A is a 3-dimensional plot of candidate (grey) trajectories and an optimal (black) trajectory. FIG. 12B is a projection of all trajectories onto a couch-gantry plane.

FIG. 12C is a projection of all trajectories onto a collimator-gantry plane.

FIG. 13A is a 3-dimensional plot optimal trajectory. FIG. 13B is a projection of the trajectory onto the couch-gantry plane. FIG. 13C is the projection of the trajectory onto the collimator-gantry plane.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Figure 1:
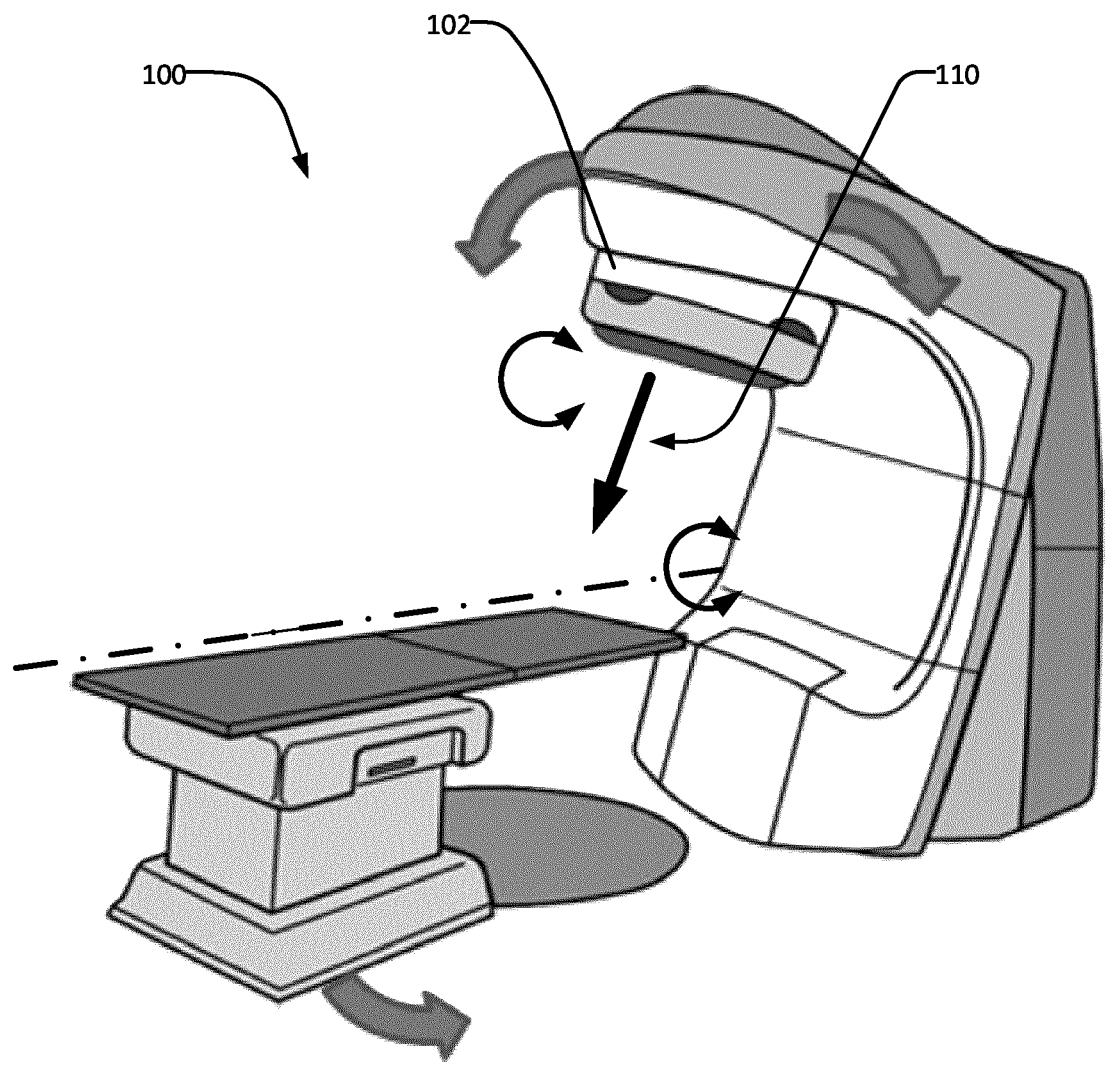
FIG. 1 is a schematic illustration showing an example radiotherapy device of a type which is commercially available.

FIG. 1 shows an example radiotherapy device 100 of a type that may be used for performing radiotherapy. The example device includes a gantry 102, which houses a radiation source (e.g. a linear accelerator) that can be controlled to emit a radiation beam 110 toward a patient. Motors (not shown) may be provided to rotate the gantry 102, and thereby rotate the point of origin of radiation beam 110 in an arc around the patient. Radiotherapy devices that are generally like device 100 are commercially available from companies such as Varian and Elekta.

Figure 2:
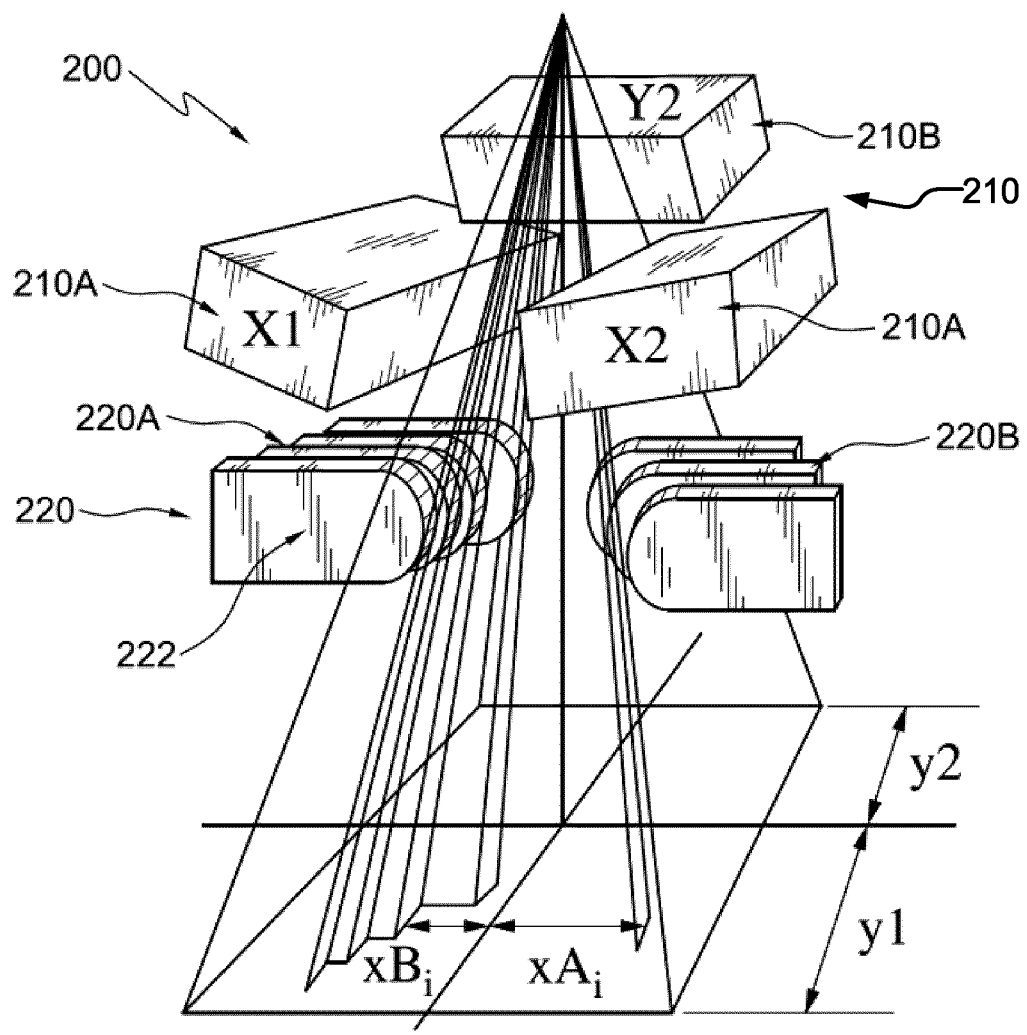
FIG. 2 is a schematic illustration showing an example multi-leaf collimation system.

FIG. 2 shows an example beam shaper 200 that includes a jaw system 210 and a MLC 220. Jaw system 210 comprises two sets of orthogonally positioned jaws 210A and 210B (only one of jaws 210B is shown in FIG. 2). Jaws of sets 210A and 210B may be positioned to shape a radiation beam into a rectangular shape. MLC 220 comprises two banks 220A and 220B of collimator leaves 222. Corresponding ones of leaves 222 from banks 220A and 220B may be advanced toward one another or retracted away from one another. Each of collimator leaves 222 may be independently positioned to shape the aperture through which the radiation beam will pass.

One aspect of the technology described herein considers how best to take advantage of multiple degrees of freedom of motion of a radiation source relative to a patient to deliver a prescribed radiation dose to one or more target volumes while minimizing radiation dose to non-target volumes and especially minimizing radiation dose to OARs. A non-limiting example case where plural degrees of freedom are available is a radiotherapy device of the type illustrated in FIG. 1 which allows movement of a couch to different couch angles as well as rotation of a gantry that carries a radiation source to different gantry angles. This problem may be made more complicated for various reasons which may include one or more of:

- some combinations of couch and gantry angles may not be allowed (e.g. because the radiation source and couch might interfere with one another or the radiation source may get too close to the patient for some combinations of couch and gantry angles).
- there may be constraints on how the degrees of freedom may be exercised (for example, some radiotherapy devices allow couch and gantry angles to be set but do not allow simultaneous dynamic changes to couch and gantry angles).
- there may be constraints on the number of trajectories and/or the types of trajectories that are allowed (e.g. it may be desired to perform optimization using a system that is limited in the number of discrete trajectories and/or the types of trajectories that can be handled-some treatment planning systems that may be used for optimization can only handle trajectories that are arcs having at least a minimum length and/or can only handle up to a predetermined number of arcs in one treatment plan which is to be optimized).

Methods and apparatus according to some embodiments prepare a multi-dimensional cost space. Preferably, the cost space has one dimension for each degree of freedom being considered. For example, a cost space for a case where a radiotherapy device has three degrees of freedom such as gantry angle, couch angle and collimator angle could apply a three-dimensional cost space or cube. A cost space may also be called a combined optimization of dynamic axes (CODA) cube.

Figure 3:
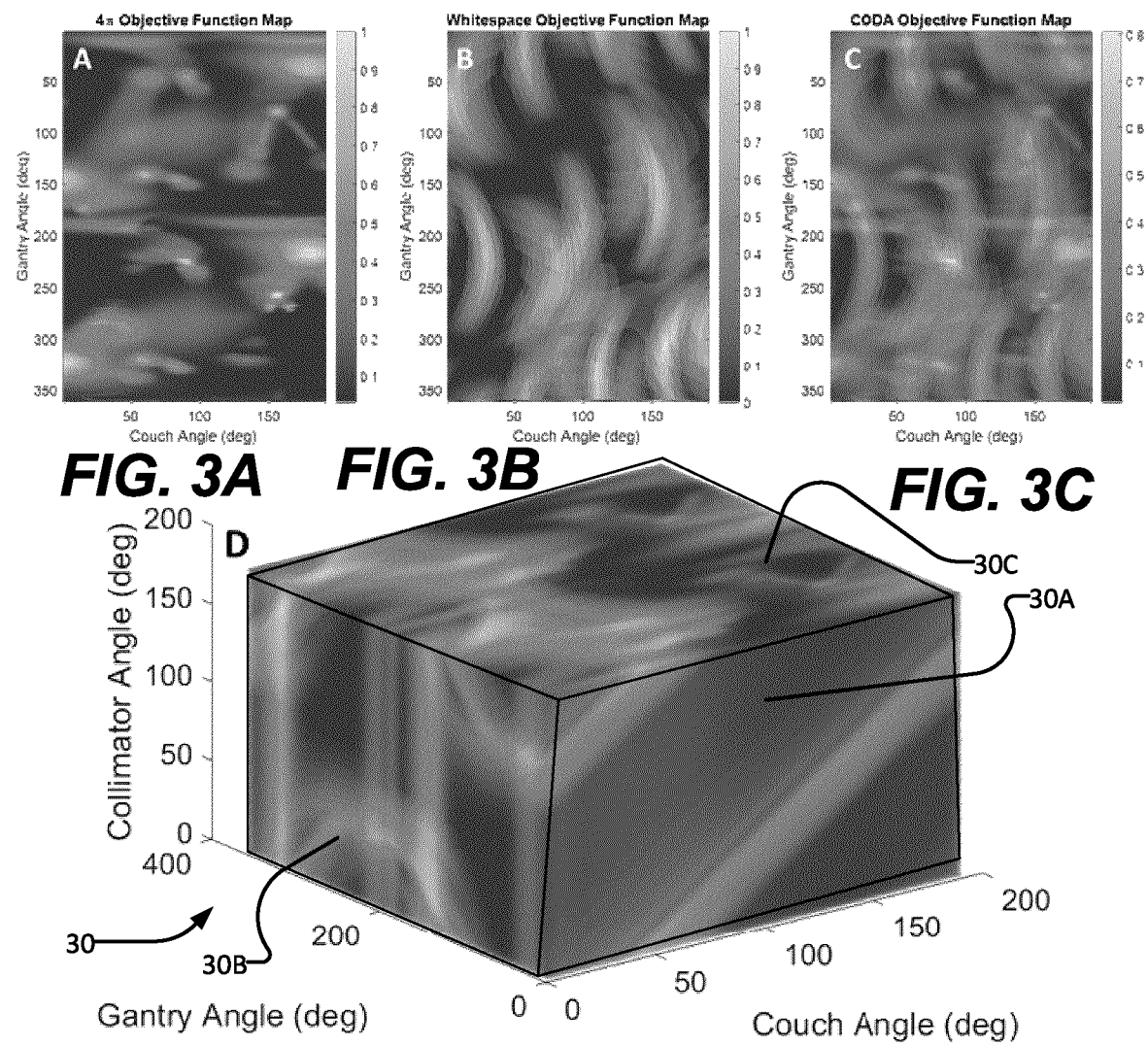
FIG. 3 is a schematic view of an example cost space.

The following discussion uses the example case of a radiotherapy device which has three degrees of freedom, specifically a gantry angle, couch angle and collimator angle. However, these examples can be readily generalized to different degrees of freedom. Additionally, or alternatively, these examples can be readily generalized to a different number of degrees of freedom (e.g. 4 or more degrees of freedom). For the example case, the cost space can be visualized as a three-dimensional cube. An example three-dimensional CODA cube 30 is shown in FIG. 3.

The cost space may be discretized (e.g. divided into voxels). In some such embodiments each voxel corresponds to a particular combination of positions of the available degrees of freedom (e.g. a particular gantry angle, couch angle and collimator angle). The voxels in cube 30 lie in planes parallel to faces of the cube. In each plane, the value corresponding to one degree of freedom is fixed. For example:

- in planes parallel to face 30A of cube 30 the gantry angle is fixed.
- in planes parallel to face 30B of cube 30 the couch angle is fixed.
- in planes parallel to face 30C of cube 30 the collimator angle is fixed.

Positions along the axes of cube 30 correspond to different values of gantry, couch, and collimator rotation angles.

Each point in the cost space may be associated with a corresponding value of a cost function. The cost function may be based both on the geometry of target region(s) and on the geometry of the radiotherapy device to be used to deliver radiation.

The cost space may be represented in a data structure, such as a suitable array that comprises memory locations for storing the cost function values which are each explicitly or implicitly associated with the location (e.g. voxel) in the cost space to which they correspond.

A wide range of cost functions is possible. The cost function is preferably selected to:

- increase costs when the voxel corresponds to a configuration that will deliver more radiation dose to OARs.
- increase costs where the voxel corresponds to a configuration that will deliver more radiation dose to non-target tissues.
- assign costs in such a manner that facilitates more efficient delivery of radiation (e.g. fewer monitor units of radiation delivered to achieve the prescribed radiation dose to the target region(s)).

In some embodiments the cost function comprises plural objective functions. Outputs of the objective functions may be combined to yield the cost function. For example, outputs of a first objective function (FIG. 3A) may be combined with outputs of a second objective function (FIG. 3B) to yield outputs of the cost function (FIG. 3C).

Figure 4:
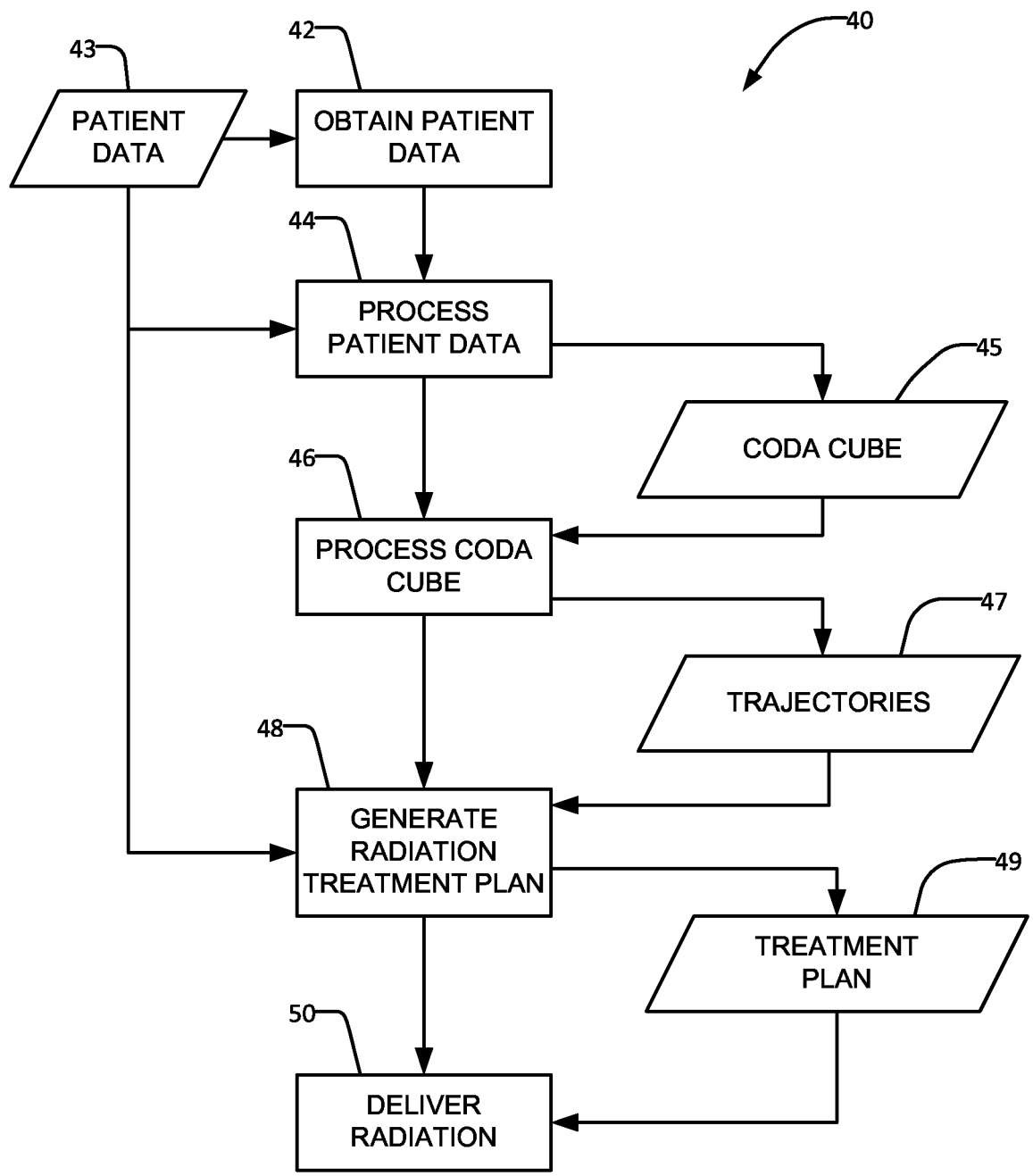
FIG. 4 is a flow chart illustrating a method according to an example embodiment.

FIG. 4 is a flow chart which illustrates at a high level a method 40 according to an example embodiment. In block 42, patient data 43 is obtained. Patient data 43 may specify bounds of one or more target volumes. Optionally, patient data 43 specifies bounds of one or more OARs. Patient data 43 may also include other information. For example, the patient data may specify outer bounds of a patient (information regarding the outer bounds of a patient may be used, for example, to prevent collisions between the patient and radiotherapy device 100—for example by ensuring that trajectories that would result in collisions or very close encounters between radiotherapy device 100 and the patient are avoided).

In block 44, the patient data is processed to yield cost function values which are stored in a data structure to provide a CODA cube 45. In block 46, the CODA cube is processed to identify a set of trajectories 47 (which may comprise arcs) to be used for delivering the radiation treatment. In some embodiments the trajectories are arcs. In some embodiments the trajectories are obtained by applying a system of graph theory algorithms to yield an optimal set of arcs or other trajectories. In block 48, the trajectories are processed together with the patient data to yield a radiation treatment plan 49. Radiation treatment plan 49 may specify parameters such as collimator leaf settings, rate of change of different degrees of freedom (e.g. gantry angle and/or couch angle), fluence, etc. for points along the trajectories. The radiation treatment plan may comprise a set of commands that may be applied by a control system of a radiotherapy device to deliver radiation treatment according to the plan. In block 50, radiation treatment is delivered according to the treatment plan. Block 50 may involve the control system of the radiotherapy device automatically executing commands of the radiation treatment plan.

In some embodiments identifying the trajectories involves identifying a number of candidate trajectories and selecting a subset of the candidate trajectories to be used for the radiation treatment plan. For example, candidate trajectories may be generated using a modified constrained Bellman-Ford algorithm to suggest a number of low-cost fixed candidate arcs on each plane of the cost space. From the resulting collection of candidate arcs, a desired number of arcs may be selected, for example, using a clustering algorithm to associate the candidate arcs to clusters and then selecting one or more arcs from each cluster. For example, a k-means clustering algorithm may be used to cluster the candidate arcs.

Optimization

In some embodiments block 48 is implemented using commercially-available treatment planning software such as Eclipse™ treatment planning software available from Varian Medical Systems or Brainlab Elements™ Cranial SRS software available from Brainlab. Block 48 may perform inverse-optimization according to clinical standards.

Some embodiments advantageously provide compact radiation dose distributions by optimally sampling the 4π space (described elsewhere herein). Automated trajectory planning as described herein may reduce non-target tissue radiation doses by avoiding BEV overlap with OARs and improve monitor unit (MU) efficiency through collimator angle optimization. Trajectories obtained using methods as described herein may improve the dosimetric properties of VMAT plans.

Specific example embodiments will now be described to illustrate applications of the present technology.

CODA Cube Construction

To measure a patient-specific solution space, a three-dimensional CODA cube may be constructed with dimensions equal to the entire range of motion for the three axes being optimized: gantry, couch, and collimator rotation angles. For every possible combination of positions along these three axes, a corresponding voxel is associated with a cost function value to quantify the suitability of including this combination in a radiation treatment plan.

In an example embodiment, the cost function is constructed by combining a plurality of objective functions. The objective functions may focus on different goals. For example, one objective function may focus primarily on decreasing radiation dose to OARs and another objective function may focus primarily on MU efficiency and reducing radiation dose to non-target tissues (e.g. healthy brain tissues, etc.). A non-limiting example embodiment provides a cost function that combines the 4π objective function (described for example in PCT international patent publication WO 2016/008052 A1 and in reference [6]), used to reduce radiation dose to OARs, and the whitespace objective function (as described for example in PCT international patent publication WO 2017/152286 A1 and in reference all of which are hereby incorporated herein by reference for all purposes) used to increase treatment plan MU efficiency and reduce radiation dose to non-target tissues.

4π Objective Function

The 4π objective function is computed from the OAR and target volume (PTV) constituents of the BEV. In some embodiments, at every coordinate of couch and gantry rotation angle the total cost, E (c,g), is computed from Equation 1:

$$E(c, g) = \sum_i w_i \left[ w_F \left( \frac{PDD(d_i)}{PDD(d_t)} \right)_{c,g} \times w_O \left[ \frac{L_i(c, g)}{A_t(c, g)} \times \frac{L_i(c, g)}{A_i(c, g)} \right] \right] + w_U \cos^n(\alpha) \quad (1)$$

In Eqn. (1), $w_i$ is a relative weighting associated with each OAR (e.g. a tolerance radiation dose for the OAR in question); $PDD(d_i)$ and $PDD(d_t)$ are the values of the percent dose deposition (PDD) curves for the treatment beam to be used (e.g. a 6 MV beam with field size 10×10 cm² and source to surface distance (SSD) of 100 cm at the depths $d_i$ and $d_t$, respectively); $d_i$ is a depth of the $i^{th}$ OAR and $d_t$ is a depth of the PTV; c and g are the couch angle and the gantry angle respectively; $L_i(c,g)$, $A_t(c,g)$, $A_i(c,g)$, are the area in the BEV as projected onto a plane at isocentre of the overlap between the PTV and the $i^{th}$ OAR, the area of PTV, and the area of the $i^{th}$ OAR, respectively; and α is the three dimensional angle between the vector joining the center of mass (COM) of the PTV and the source position, and the vector joining the COM of the PTV with the COM of the OAR deemed most urgent for sparing (e.g. an OAR that is closest in proximity to PTV or an OAR that is especially sensitive). $w_F$, $w_O$, and $w_U$ are weighting coefficients for terms in the 4π cost equation. These weighting coefficients may be assigned equal values or may be assigned unequal values to emphasize some terms of Eqn. (1) more than others.

4π objective function maps are measured for every combination of PTV and OAR and summed based on the designated weighting values as depicted in Eqn. (1).

Various means may be used to project the PTV(s) and OAR(s) into the isocentre plane. For example, previously published in-house MATLAB (The MathWorks, Inc., Natick, Massachusetts, USA) software, which extracts structure information from RT structure set DICOM files and simulates the BEV for a given couch and gantry position may be used for this function.

The objective function values may be catalogued into a map in which the full range of the couch rotation axis (e.g. 191 degrees) and gantry rotation axis (e.g. 360 degrees) are measured. Coordinates which correspond to a physical collision of the gantry and the couch or the gantry and the patient may be assigned very high or infinite costs to prevent their inclusion in a trajectory. Coordinates of the collision space (e.g. combinations of couch and gantry angles that should be avoided) may be manually measured on a radiotherapy device to be used for delivery of radiation treatment. In some embodiments these coordinates are recorded in a data store.

For example, a prototype embodiment was implemented using a Varian TrueBeam STx™ (Varian Medical Systems, Inc., Palo Alto, CA, USA) linear accelerator at the Nova Scotia Health Authority (NSHA). An anthropomorphic phantom was placed on the couch, and the couch was placed at typical coordinates for a cranial treatment: longitudinal position of 90.85 cm, a vertical position of 15.00 cm, and a lateral position of 0.00 cm. The gantry and couch were rotated over their full ranges of motion. A point in a collision zone was recorded for which the couch position and gantry position were such that: (a) the collision avoidance system of the TrueBeam™ was triggered; or (b) the gantry was within a 5 cm buffer to either the treatment bed or the anthropomorphic phantom.

Whitespace Objective Function

A whitespace objective function may be used to optimize the collimator rotation angle, and by consequence, the direction of MLC leaf travel. The whitespace objective function quantifies the area of non-target anatomy (non-target tissues) left uncollimated in the BEV when the MLC is fit conformally to the target. By categorizing and measuring these areas in any BEV defined by the couch rotation angle ($\theta_{CH}$), gantry rotation angle ($\theta_{GA}$), and any chosen collimator angle ($\theta_{CL}$), the parameter denoted by whitespace (W) can be defined, for example, by Equation 2:

$$W(\theta_{CL},\theta_{CH},\theta_{GA})=w_1 A_{Jaw}-w_2 A_{PTV}+w_3(A_{PTV} \cap A_{OAR})-w_4 A_{MLC} \qquad (2)$$

In Eqn. (2): $A_{Jaw}$ is the area collimated by the fitted rectangular jaws, $A_{PTV}$ is the area of the PTV, $A_{PTV} \cap A_{OAR}$, $A_{OAR}$ is the area of the OAR overlapping with the PTV, and $A_{MLC}$ is the area collimated by the MLC in a conformal position when the entire PTV is targeted. The variables $w_1$, $w_2$, $w_3$, and $w_4$ are weighting coefficients to control the significance of each term. These coefficients may be the same or may be given different values to emphasize one or more terms of Eqn. (2) over other terms of Eqn. (2).

The whitespace may depend on the design of the MLC or other beam shaper used to shape the beam. The MLC may be modeled, for example, using vendor specifications for leaf number and width. This model of the MLC may be used to determine MLC leaf positions for each BEV.

The whitespace output from Eqn. (2) may be catalogued into a three-dimensional space (whitespace cube) in which whitespace values for the full range of couch axis (e.g. 191 degrees), full range of gantry rotation axis (e.g. 360 degrees), and full range of collimator rotation axis (e.g. 180 degrees) are recorded.

In the prototype embodiment, the MLC used was a Varian model HD 120 (Varian Medical Systems, Inc., Palo Alto, California, USA). The HD MLC 120 has two bi-lateral banks of leaves, each composed of sixty individually positionable tungsten leaves. The central 32 pairs of leaves have a 2.5 mm width and the peripheral 28 leaf pairs have a 5 mm width when projected to isocentre.

Combined Objective Function

In embodiments in which the cost function comprises plural combined objective functions the objective functions may be combined in various ways. These include, for example, one or a combination of:
  summing;
  averaging;
  sum of squares;
  weighted averaging;
  taking a maximum;
of the plural objective functions. Typically, it is desirable to normalize each of the objective functions prior to or as part of the process of combining the objective function values.

In some embodiments the combination of objective functions is defined in part by the nature of the PTVs. For example, where the PTVs are concentrated (as, for example in the case of a single spherical PTV) it may be desirable to weight an objective function that measures radiation doses to OARs (e.g. a 4π objective function) more heavily whereas in a case where plural PTVs are distributed it may be desirable to weight an objective function that measures the ability of a beam shaper to fit to the PTVs (e.g. a whitespace objective function) more heavily. In some embodiments objective functions are combined by weighted averaging. In some embodiments weights are determined by processing projections of PTVs (or PTVs and OARs) in the BEV.

In an example embodiment, to merge the 4π and whitespace objective functions, the two-dimensional couch-gantry planes of the whitespace cube are extracted such that each plane has an iso-collimator angle, and the mean of every couch-gantry pixel is taken between the 4π and whitespace values. The resulting averaged two-dimensional objective function planes are then used to construct the combined three-dimensional CODA cube. The results of combining objective functions on a single plane into an example CODA cube are shown in FIG. 3.

FIGS. 3A, 3B and 3C illustrate one way in which a plane of the CODA-cube can be constructed. These figures respectively show an example single plane of a 4π objective function map for all target volumes and OARs included in the optimization; a couch-gantry plane of the whitespace cube taken for a single collimator angle; and a pixel-wise mean of the planes shown in FIGS. 3A and 3B.

In FIG. 3A, the 4π objective function is calculated for every couch and gantry combination. The 4π objective function quantifies the beam angles' impact on OARs for every couch and gantry angle. FIG. 3B shows the collimator objective function (whitespace) map calculated for every couch and gantry combination at one collimator angle. The whitespace function quantifies the amount of non-target anatomy left uncollimated in a conformal MLC setting and is quantified for every BEV. FIG. 3C shows the mean value of 4π and collimator objective functions at every couch and gantry combination to create one plane of the CODA cube shown in FIG. 3. Each voxel of the CODA-cube represents the relative suitability of a particular beam angle for use in a radiotherapy trajectory.

A trajectory 51 (see FIG. 5) may, for example, be calculated from optimal minimum-cost fixed arcs for traversing the CODA-plane. These arcs may be passed to candidate arcs (see FIG. 6).

CODA Cube Navigation

A CODA cube as described herein may be applied to design optimal trajectories (arcs or otherwise) for use in radiotherapy treatment planning. Contiguous voxels of low cost in the CODA cube represent potential paths for a radiotherapy device to follow. For example, trajectories designed in a CODA cube may correspond to arcs which may be used in VMAT planning for cranial stereotactic radiosurgery.

In some embodiments data defining the trajectories is provided as an input to a planning tool. For example, for VMAT planning a commercially available planning tool such as Eclipse™ may be used. In some embodiments generation of the trajectories is performed in a way that causes the trajectories to satisfy constraints of the planning system. Examples of constraints that may be imposed include one or more of:
  maximum number of trajectories;
  minimum length of trajectories;
  requirement that trajectories have a particular form (e.g. the trajectories may be required to be arcs of a particular type, such as for some cases the couch angle may be required to be constant for each trajectory involving gantry rotation);
  etc.

For example, for the VMAT optimizer PRO v. 11.0.31 from Varian Medical Systems Inc., of Palo Alto, California, USA the total arc gantry travel length for each arc must be at least 30 degrees and there can be no more than 10 arcs in the final arc solution.

Finding all allowable trajectories and identifying the optimal set of trajectories for a patient-specific CODA cube may be expressed in graph theory notation by the following four expressions:

$$S = \min \Sigma_{(i,j) \in E} c_{ij} x_{ij} \quad (3)$$

$$(i-j) \geq L_{min} \quad (4)$$

$$\Sigma_{(i,j) \in E} x_{ij} \leq N_{max} \quad (5)$$

$$(i, j) \in Z;\ i < j \quad (6)$$

where S is the final arc solution; $c_{ij}$ is the cost of an arc beginning at gantry angle i and ending at gantry angle j; $x_{ij}$ is a binary property of arc $c_{ij}$, where $x_{ij}=1$ indicates that it is part of the final arc solution and a 0 if it is not; $L_{min}$ is the minimum allowed arc length and $N_{max}$ is the maximum allowed number of trajectories. Additional restrictions that may be imposed include requiring only fixed couch and collimator geometries due to current LINAC hardware and software limitations (i.e. requiring that rotation angle of one of these axes can be defined only once per arc).

Imposing restrictions on allowable trajectories while processing the CODA cube reduces the solution space and may make finding the optimum trajectories more computationally efficient.

With these restrictions, an example procedure for defining an optimal set of arcs for a given CODA cube may comprise: (1) finding the optimal set of allowable minimum cost arcs for traversing a given couch-gantry plane; (2) accumulating all couch-gantry plane solutions into a set of candidate arcs; (3) separating arcs into spatially distributed clusters (e.g. by use of a k-means clustering algorithm); and (4) selecting the arc with longest total gantry span from each cluster to be used in the final solution.

Generation of Candidate Arcs

To find the optimal set of allowable minimum-cost arcs, a set of candidate minimum-cost arcs may be constructed. In an example embodiment this is done by independently solving each couch-gantry plane of the CODA cube. Each plane may be solved for the optimal set of minimum-cost arcs which compose a piece-wise function that spans the gantry domain (see for example FIG. 5) and is allowed by chosen treatment planning software.

Figure 5:
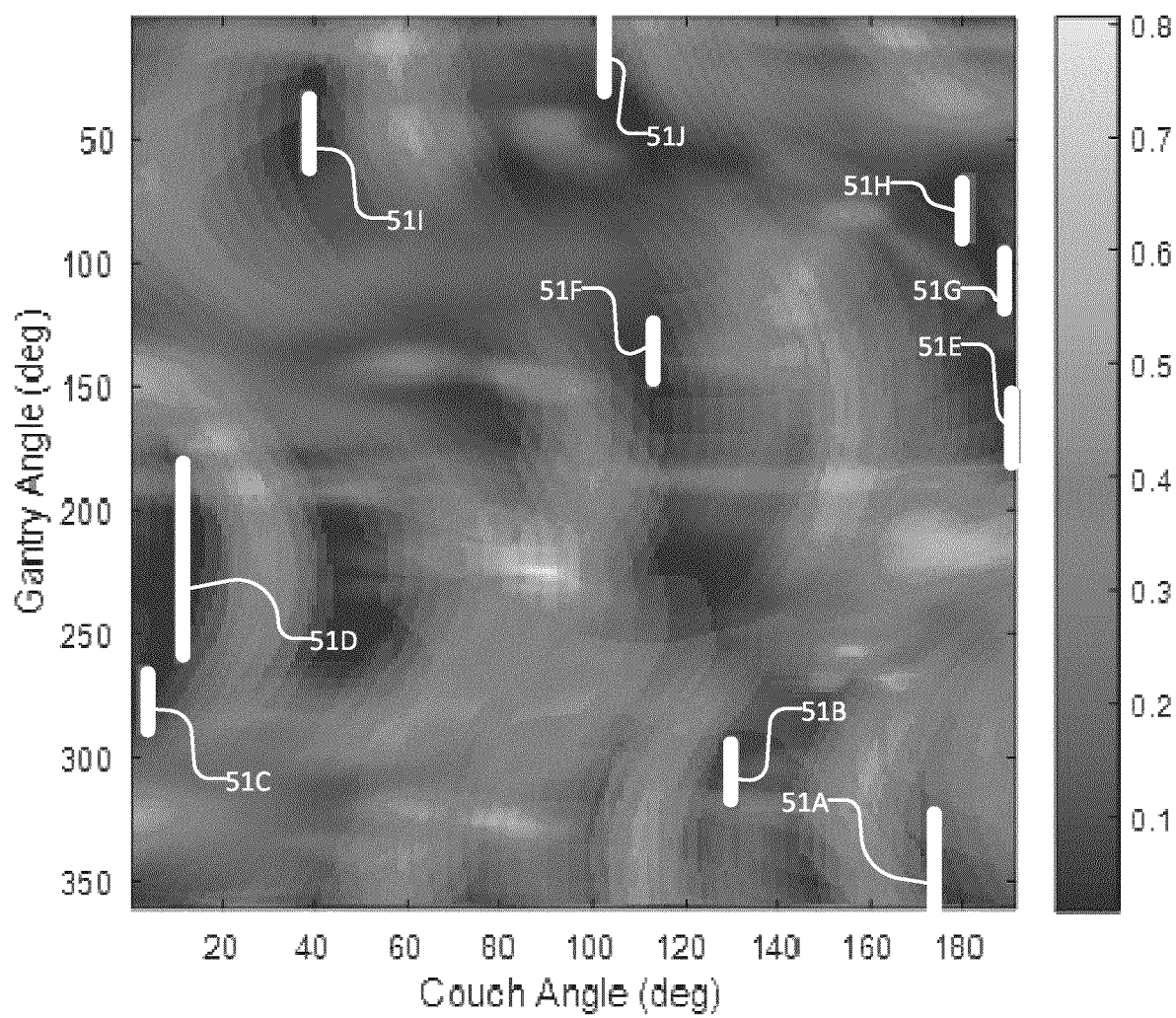
FIG. 5 illustrates a set of candidate trajectories generated by solving one plane of a CODA cube.

FIG. 5 shows one couch-gantry plane of a CODA cube for a single collimator angle as shown in FIG. 3C. Line segments 51A to 51J (collectively segments 51) correspond to the minimum cost piece-wise function trajectory with ten or fewer arcs that spans the complete range of gantry angles. Line segments 51 may be constructed to completely cover the full range of gantry angles without overlapping.

To solve a couch-gantry plane, a collection of all possible arcs within the plane may be assembled. For all arcs, $c_{ij}$, starting at gantry angle i and ending at gantry angle j, the minimum-cost couch angle may be identified, min $(c_{ij})$. The min $(c_{ij})$ arcs may then be matched into combinations that form piece-wise functions spanning the gantry domain. The minimum cost piece-wise function that uses the least number of arcs may be determined, for example, using a modified constrained Bellman-Ford algorithm. In the example illustrated by FIG. 5, a maximum of 10 arcs was permitted.

When all planes have been independently solved, the plane solutions (in this case each plane solution is for a corresponding collimator rotation angle) are compiled to generate a complete set of low-cost candidate arcs from which a final arc solution set may be chosen.

Figure 6:
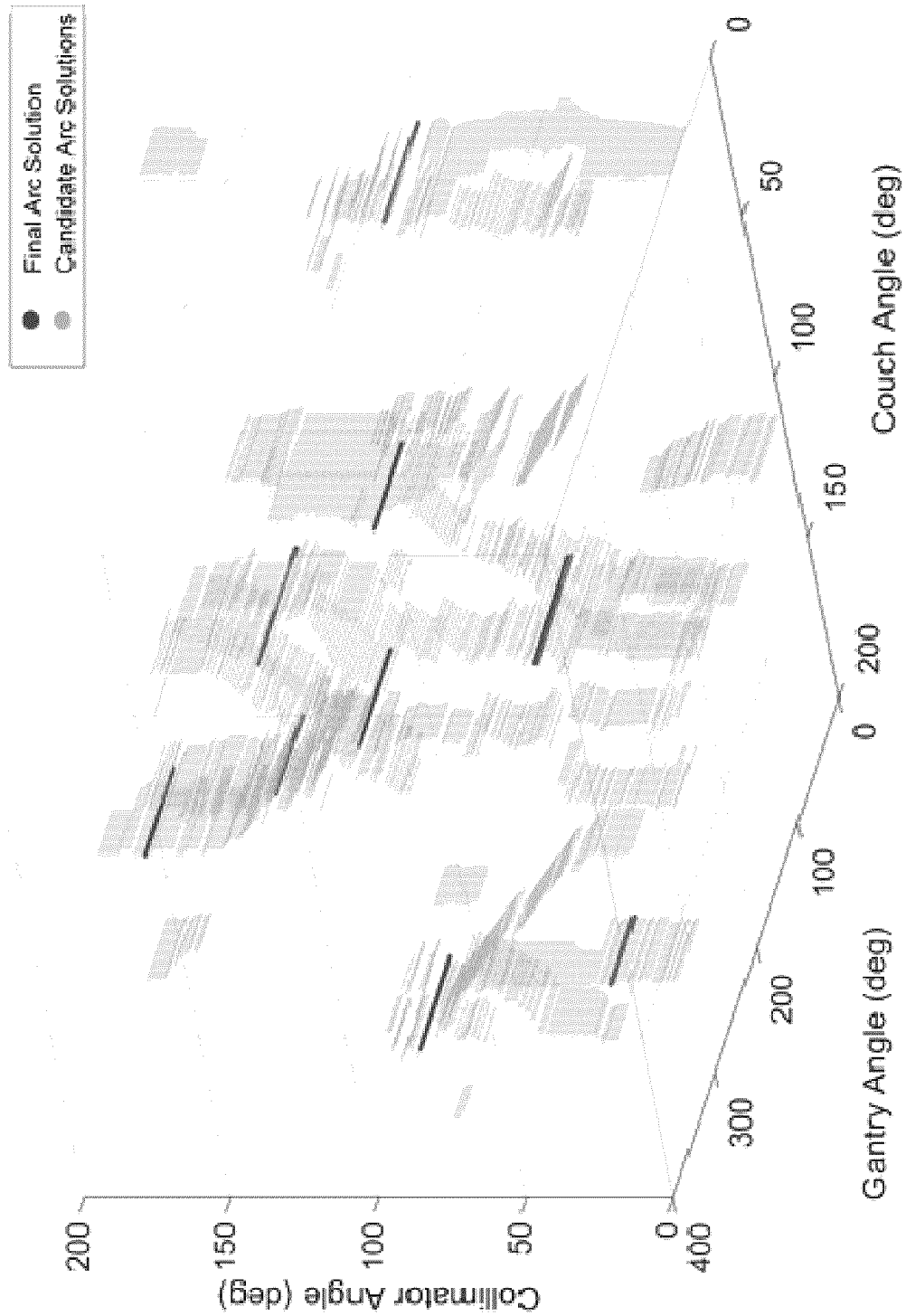
FIG. 6 illustrates a complete set of candidate trajectories in a CODA cube and a final set of trajectories selected from the candidate trajectories.

FIG. 6 shows all candidate arcs generated for the CODA cube shown in FIG. 3.

Final Arc Solution Selection

The set of candidate arc trajectories is made from low-cost solutions to the couch-gantry planes of the CODA cube. Clustering may be used to define the selected set of arcs that compose the final arc solution. In an example case, the average gantry position and couch position for each arc may be input into a k-means clustering algorithm to identify ten clusters of candidate arcs which are spatially separated in the couch-gantry dimensions. A criterion may be used to select one arc from each cluster. For example, the arc with the longest total gantry span may be selected for use in the final arc solution. Using the longest gantry span as a criterion is advantageous because that choice of criterion will yield a final set of arcs that maximizes the total number of control points in the final arc solution, thereby increasing the potential for the radiation dose optimizer to identify opportunities to improve target conformity.

Example Clustering Algorithm for CODA.

A k-means algorithm may create k spatial clusters from input data by iteratively refining minimum distance centroids for all points within a cluster. Clusters may be iteratively revised in order to stratify input data into optimal clusters which minimize the distance from a given cluster's data to its centroid. The k-means algorithm is a general and well-known algorithm. The k-means algorithm is a convenient way to recognize spatially separated groups of arcs. A reference that describes the k-means clustering algorithm is Tapas Kanungo et al. *An Efficient k-Means Clustering Algorithm: Analysis and Implementation*, IEEE TRANSACTIONS ON PATTERN ANALYSIS AND MACHINE INTELLIGENCE, VOL. 24, NO. 7, July 2002, which is hereby incorporated herein by reference for all purposes. The value of k may be chosen to equal the number of trajectories that it is desired to generate.

Alternative methods could be used to group candidate arcs or other candidate trajectories into clusters. Such alternative methods include:
 brute force sorting;
 K-Medians clustering;
 Mean-Shift Clustering;
 Density-Based Spatial Clustering of Applications with Noise (DBSCAN);
 Expectation-Maximization (EM) Clustering using Gaussian Mixture Models (GMM);
 Top Down Agglomerative Hierarchical Clustering;
 Bottom Up Agglomerative Hierarchical Clustering;

To define the selected set of arcs that compose the final arc solution, the arcs may be associated with their respective centre of mass (COM) positions within the CODA-cube space. This is different from the COM in radiotherapy coordinate-space. This involves identifying the mean gantry position, mean couch position, and mean collimator position for each arc. One can then ignore the collimator angle and consider only the COM couch and gantry positions corresponding to each arc. Only couch and gantry positions represent the location in the 4π (couch and gantry) space.

The resulting 2D CODA-space COM arc-coordinate may be entered into the k-means clustering algorithm with all other arc-coordinates in order to identify a desired number of clusters (for example 10 clusters or a maximum number used by the planning system) of candidate arc coordinates which are spatially separated from one another in the couch-gantry plane.

Each of the arcs inside of each of the clusters may be sorted by their initial total gantry range. The arc having the longest spanning gantry arc within each cluster may be selected as the representative arc for the cluster. Performing this for every cluster yields one arc from each cluster, with the longest cluster-local gantry travel, which ought to be maximally diverse in the 4π couch-gantry space from clustering the 2D COM of the arcs.

Example Plane-Based Solution Method

The following is a detailed example implementation of a method according to some example embodiments.

Once a CODA cube has been created, identifying sets of trajectories can be seen as a shortest path problem (one can consider values of the cost function as a generalized 'distance'). There are a range of known algorithms for solving shortest path problems. A number of such algorithms construct graphs by building edges (arcs) between points and all adjacent points on the integer lattice, effectively creating an integer grid which can be traversed from some starting point to some ending point. If the optimal starting and ending points are not initially known then the shortest path algorithm may consider all combinations of starting and ending points to obtain a global optimal path solution.

The addition of constraints complicates solving a shortest path problem. Many known shortest path algorithms cannot handle certain types of constraints. In at least some embodiments of the present technology, it is desirable to impose constraints such as:

1) a maximum number of arcs can be used to span the range of gantry angles.
2) all arcs must have lengths of at least a minimum length.

These constraints may, for example, be determined by software and hardware capabilities of a radiation treatment planning system and/or a radiotherapy device to be used.

Some embodiments generate only graphs that contain arcs (edges) that satisfy constraint 2) described above. Such embodiments do not need to generate the full integer lattice of possible arcs but only generate arcs that are deliverable on an available radiotherapy device. This has a two-fold effect of allowing the use of some shortest path algorithms and making the algorithm faster as arcs that don't comply with the constraints are not considered.

Some embodiments also exploit the fact that for any gantry span (e.g. 0-30 degrees) there is a unique couch angle for which a minimum cost arc can be found. These arcs are referred to as the minimum convex set of arcs or the dominate set of arcs as they dominate any other arc with a gantry start value of 0 degrees and a gantry end value of 30 degrees, and couch value between 0 and 180 degrees. Pre-filtering the set of arcs to the dominate set may drastically reduce the number of arcs to be considered. For example, such prefiltering may reduce the number of arcs to be considered from approximately 8 million to a set containing just 60,000 arcs. An added advantage of using the dominate set is that it only contains one start point and one end-point, making it unnecessary to run a shortest path algorithm with all possible starting and ending points. This may lead to a faster planning time.

Due to performance, Dijkstra's shortest path algorithm is typically used to solve similar shortest path problems but Dijkstra's algorithm becomes infeasible when constraint 1) described above is imposed. Typical implementations of the Bellman-Ford shortest path algorithm will not only be slower than Dijkstra's shortest path algorithm but cannot be used to solve problems that have a constraint similar to constraint 1).

Some embodiments leverage the sequential nature of the Bellman-Ford algorithm to not only comply with constraint 1), but also to only add arcs to the final solution when the accumulated score is decreased. In other words, given two solutions of sets that contain no more than a maximum number of arcs, the solution that contains fewer arcs is preferred as this solution is currently easier to deliver clinically. By its nature, the Bellman-Ford algorithm recursively solves shortest path sub problems by considering the shortest paths for all intermediate nodes (points in the integer lattice) on the way from the starting point to the ending point, if known.

The modified constrained Bellman-Ford algorithm used in the example algorithm described herein utilizes the dominate set of arcs and recursively finds the shortest path to intermediate nodes from starting to ending point while making sure to comply with constraint 1). This not only leads to compliance with constraint 1), but also shortens optimization time as only x number of edges for each intermediate node are used. This algorithm may be expressed using the following pseudo code:

Input: An m×n map of score values indicating the cost incurred to move from a point to an adjacent point.

Output: No more than x arcs are used that are all greater than or equal to y degrees in length and span the entire gantry (m) dimension.

Steps:

Step 1) Generate all integer length arcs by summing map score between every combination of gantry points that can be realized within software/hardware limitations of a radiotherapy device.

Step 2) Find the dominate (minimum convex) set of arcs. Given a unique span of gantry (for example 0-30 degrees) there is only one unique couch angle that minimizes cost over that gantry span. All other arcs of the same gantry span are not used because their use would lead to a suboptimal solution.

Step 3) Solve the graph containing only the dominate set of edges using the modified Bellman-Ford algorithm terminating when constraint 1) is realized for each recursive intermediate node. Combine intermediate node solutions to find a set of arcs that spans the m dimension of the input map and complies with constraint 1).

Detailed Description of Example Step 1: Construction of the CODA Cube

Efficiencies in constructing a CODA cube may be achieved by importing only relevant anatomical contours from patient data (e.g. from a treatment planning system) to efficiently model the relevant patient geometry. This may involve, for example:

Identifying anatomical storage locations from DICOM format structure files.

Parsing relevant information for structure boundaries and locations.

Automatic identification of structure types (e.g. 'target', 'organ at risk') to appropriately enter the structure into the optimization.

Adding property 'USF' to organ at risk defined by the user for entry into urgent sparing factor calculation.

Adding property "OAR weight" according to the importance of a given OAR.

Making coordinate system transformations, for example, into a defined radiotherapy coordinate system. Some treatment planning software systems that may be a source for patient data do not use consistent (or conventional) coordinate systems. In some cases purpose specific coordinate system translation may be provided.

The CODA cube may then be constructed such that axes of motion of the radiotherapy device are in a deliverable path for a continuous trajectory. For example, some radiation delivery devices may not be able to provide continuous 360 degree gantry rotation. In such devices rotation in one direction may be limited at a particular gantry angle. The limiting gantry angles for rotation in both directions may be the same or different. In such cases the CODA cube may be constructed so that all trajectories lying within the CODA cube may be delivered in a continuous movement of one or more degrees of freedom. For example, consider the case where gantry motion in both directions is limited at a gantry angle of 180 degrees. In such cases the CODA cube may be constructed such that gantry angles of 180 degrees lie on opposing faces of the CODA cube.

In some embodiments isocentre is designated at a specific location relative to the target volumes (for example at the centre-of-mass of the target volumes to be treated in the optimized plan). In some embodiments BEV metrics depend on isocentre.

For generating BEV metrics all contour information (e.g. contours of PTVs and OARs) may be projected onto a plane defined by a normal vector in the direction of the source, which intersects isocentre. Divergent projection of all contour information may be calculated with high-resolution so that the projected contours are accurate. In some embodiments values for use in BEV metrics are calculated by determining:
- the overlap between projections onto a plane (e.g. a plane at isocentre) of all structures designated as targets and all structures designated as OARs.
- the urgent sparing factor(s) for the designated OARs.

For every couch and gantry position, collimator BEV metrics may be quantified for every valid position that the collimator can hold. This may be done by:
- projecting every target structure onto a plane at isocentre.
- converting the projection into a high resolution binary mask.
- combining all target binary masks using a Boolean AND operation to yield a total binary mask.
- measuring whitespace based on the total binary mask for total whitespace at every collimator angle.

Measuring whitespace may be performed by modelling the MLC or other beam shaper and applying the model to determine a configuration of the beam shaper for conformal fitting to the binary mask for every possible collimator angle. A quantity of uncollimated non-target pixels may be identified and quantified for entry into the collimator objective function. "Whitespace" is most efficiently quantified by examining each leaf-pair range as a 1D binary profile. The boundary of the structures within this 1D profile may be designated as the outer limits of collimation. Any non-target pixels inside the profile may be counted as "whitespace".

One efficient way to construct a CODA cube involves:
1. Initially constructing the total CODA cube using whitespace for the cost function value for every position of the gantry, couch and collimator. This may be done in the specific logical delivery order previously mentioned.
2. Weighing all OAR-specific overlap maps according to the OAR with which they were measured and summed through element-wise addition to produce a total overlap map.
3. Adding the USF map to the total overlap map from the previous step to additionally add cost to the map.
4. Normalizing the total map such that the maximum value found in the map is a value of 1 (or another normalization value) and normalizing the pre-allocated CODA cube filled only with whitespace values. Normalizing the 4π and whitespace objective function output values ensures contribution from both objective functions in situations where their raw values are dissimilar.
5. Setting regions in the couch-gantry map which are not reachable (e.g. because of physical interference or collision) to have very high values (such as positive infinity).
6. Combining every plane in the 'whitespace cube' through an element-wise mean with the total 2D couch-gantry 4π map, after both have been normalized to yield the CODA-cube.

Detailed Description of Example Step 2: Solving Navigation for a CODA Plane Using a Modified Constrained Bellman-Ford Algorithm to Suggest Low-Cost Fixed Candidate Arcs on Each Plane of the Space The CODA cube (with collision zones input) is supplied along with treatment planning restrictions for minimum total gantry span and maximum number of arcs allowed in a final arc solution. Solutions (sets of trajectories) are generated for the couch-gantry planes. Gantry angle is one dimension of the couch-gantry plane. Each couch-gantry plane may be individually analyzed as follows:
- the valid start and stop positions for every possible spanning gantry arc are produced that comply with the treatment planning system restrictions.
- for any valid gantry-start-stop span, all possible couch angles are assigned and the total integrated score from an arc in this location is quantified.
- the minimum total integrated score for this gantry span is identified by its couch angle.
- to decrease the total number of arcs being analyzed, all arcs that are not the absolute minimum integrated total score over this gantry span are removed.

This process computes a "minimum convex set" of arcs which advantageously facilitates performing this optimization in a realistic time-frame. This reduces the total number of arcs to be considered by a factor of more than 100. Additionally, this removes the need to examine couch angles any further and reduces the problem to only optimal gantry start and stop angle combinations. This improves the overall efficiency of using graph theory algorithms in this application.

The complete minimum convex set may then be used (e.g. by applying the modified Bellman-Ford algorithm described herein) to compute all possible solutions to the couch-gantry plane generated with a total number of arcs spanning from 1 to a user-defined maximum number of arcs.

For every possible total number of arcs allowed in a solution (e.g. 1 to $N_{max}$), the system identifies all arcs from the minimum convex set which contiguously span the entire couch-gantry plane and sums their integrated scores.

For illustrative purposes: let the total number of arcs be 2. This means that the system would find the solution for the minimum convex set solution for the arc from gantry at 1 degree to gantry at 30 degrees and the minimum convex set solution from gantry at 31 degrees to the end of the map. It then stores the integrated value and attempts the minimum convex set solution from gantry at 1 degree to gantry at 31 degrees, and the minimum convex set solution from gantry at 32 degrees to the end of the map. As one can imagine, as one increases the total number of allowed arcs in a solution, the combinatorics become very high. Reducing this set to the minimum convex set helps to make computational solutions to the problem feasible. The output of this process may comprise a table in which all numbers from 1 up to the maximum number of arcs used to cross the map is given in the rows, and the 'node' position (any gantry angle) is given in the columns. The value in each element is the location of the preceding node (gantry angle) that the solution would have to have used as a gantry starting point in the arc that leads to the node in that column, in the solution that totals to the number of arcs in that row.

To determine the minimum number of arcs required for the final solution, one can compare the total integrated scores for each set of contiguous arcs that span the full gantry space. The final solution is the set with the minimum total integrated score and the fewest arcs.

All solutions to all couch-gantry planes within the CODA cube may then be organized into a complete set of arcs for every maximum number of total arcs in a solution.

Detailed Description of Example Step 3: Final Solution of 10-Arcs Chosen Using k-Means Clustering All solutions from all couch-gantry planes for all maximum number of total arcs in a solution may be input. For every arc, in every solution, at every plane, the arc may be separated into control points (e.g. points spaced apart at 1-degree resolution) in all axes. For each arc, the 3-dimensional COM of the arc may be taken in CODA-cube space. This is not the same as the COM in Radiotherapy coordinate-space.

The values of couch and gantry in the 3D CODA-cube COM may be retained, and the collimator location may be dropped, as only couch and gantry locations specify the address in the $4\pi$ space (couch-gantry space).

The COMs for the arcs may then be input into a clustering algorithm (e.g. k-means). For example a k-means algorithm may be applied which takes as input the 2D CODA-cube space COMs for all arcs. $N_{max}$ centroids may be produced to yield $N_{max}$ final clusters. Every arc in the solution is associated to one of the clusters (e.g. by having assigned to it a cluster index). The entire bank of all arcs may be sorted by their cluster index, followed by their total length of gantry span. For every cluster, the longest spanning gantry member may be selected and input to the final solution. The coordinates of these arcs may then be translated from CODA-cube space to suitable coordinates applicable for input to a radiation treatment planning system.

VMAT Planning & Comparison

To demonstrate patient-specific trajectory optimization using CODA, eight artificial target volumes were manually contoured using Eclipse v11. The artificial targets span the volume sizes appropriate for a radiation prescription of 24 Gy as per RTOG 9508. All radiation dose calculations were performed in Eclipse using AAA v.11.0.31 and a calculation grid size of 1.5 mm. All artificial targets were within 5 cm of an OAR, with four targets closer than 1 cm: 0.44 cm from the optic chiasm, 0.74 cm from the brainstem, 0.66 cm from the brainstem, and 0.28 cm from the brainstem.

Combinations of these targets were used to generate seven cases of three and four target geometries. Two VMAT plans were generated for each case: one using the standard VMAT cranial stereotactic arc template used at the Nova Scotia Health Authority (NSHA) (shown in Table 1), and one using the case-specific trajectory defined in CODA-cube optimization. All VMAT planning was conducted by a CMD-certified treatment planner with six years of VMAT planning experience. Most of the VMAT planning required up to four passes through the optimizer to meet OAR and PTV constraints, with adjustments on objectives and priorities on each pass.

VMAT optimization was done by the progress resolution optimization (PRO) algorithm in Eclipse (PRO v.11.0.31). Automatic normal tissue objective (NTO) was used in all cases, as well as a tuning ring around the PTVs (4 cm outer diameter, 1 cm inner diameter). All artificial targets were treated using prescription radiation doses of 24 Gy prescribed to the 90% isodose.

TABLE 1

Gantry and couch parameters for the clinical stereotactic plan used at the NSHA. CW = clockwise, CCW = counter-clockwise. These coordinates are in the IEC 1217 system.

| Couch Angle (°) | Gantry Start (°) | Gantry Stop (°) | Gantry Direction |
|---|---|---|---|
| 45 | 180 | 0 | CCW |
| 0 | 180.1 | 179.9 | CW |
| 90 | 150 | 355 | CCW |
| 315 | 0 | 180 | CW |

Metrics were extracted from all plans using MATLAB scripting. The clinically relevant metrics extracted were: total MU, brain volume receiving 12 Gy or greater, conformity index for all targets, and maximum radiation dose delivered to the brainstem, eyes, lenses, optic chiasm, and optic nerves.

Results

VMAT Planning & Comparison

FIGS. 7A to 7D, 8 and 9 illustrate the results averaged over the seven-plan cohort. The most salient planning details are shown in FIGS. 7A to 7D: a decrease in maximum radiation dose to the brainstem (the most proximal organ at risk in all cases) of 24.4% (p=0.031), a mean MU reduction of 8.6% (p=0.16), a mean V12 Gy reduction of 3.9% (p=0.16), and a 0.1% reduction in inverse van Riet conformity index (CI) with implementation of CODA. All errors are shown as standard deviation.

Figure 8:
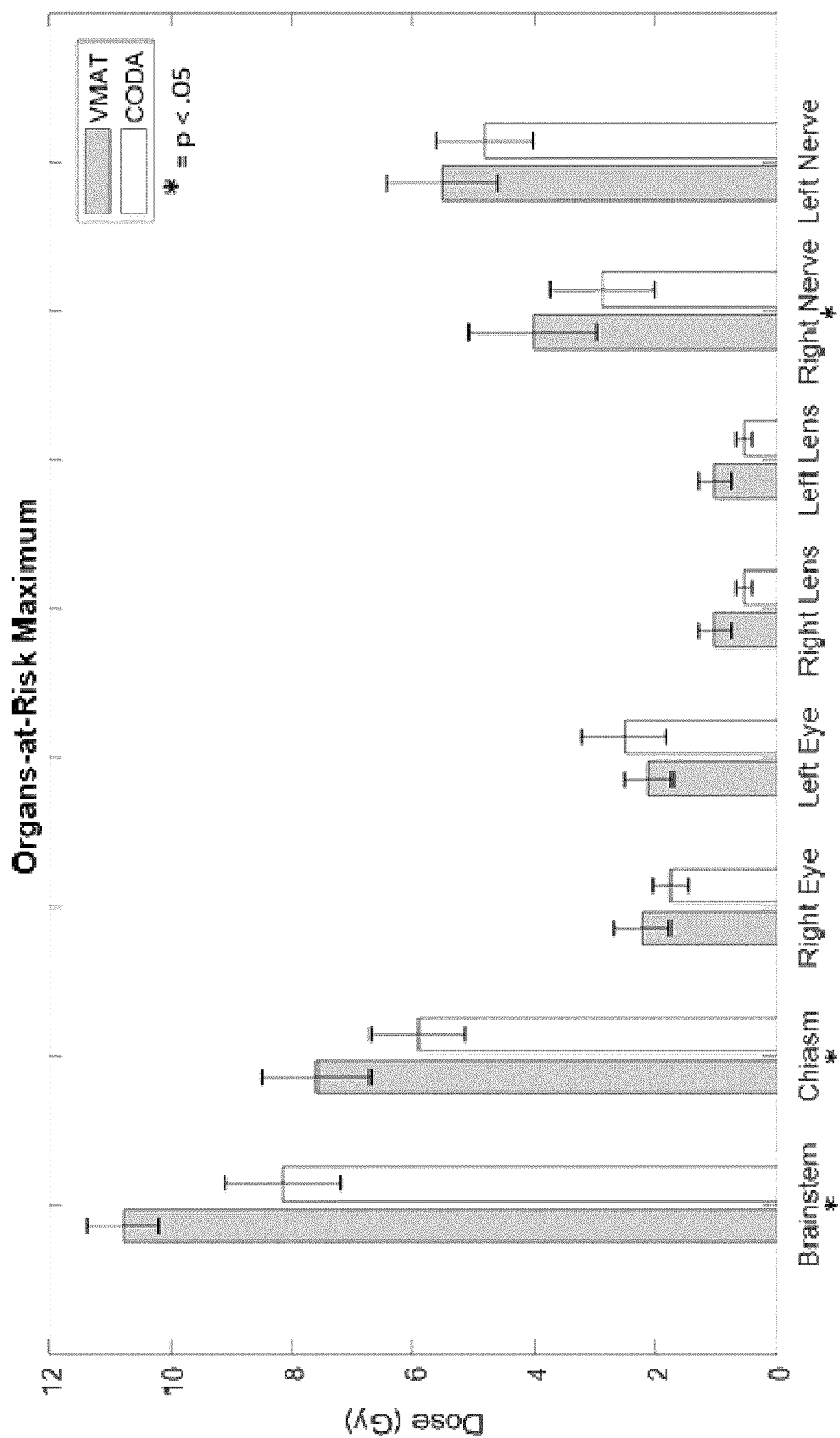
FIG. 8 shows a comparison of OARs used in the optimization of CODA trajectories in comparison of CODA and standard VMAT plans (n=7). All illustrated error bars show standard deviation.

FIG. 8 shows the mean and standard deviation values of maximum radiation doses for all OARs used in the CODA optimization and standard arc VMAT. CODA optimization decreased the maximum OAR radiation dose on average in all but one OAR, the left eye. The four OARs with the highest radiation dose on average (i.e. the brainstem, the chiasm, and the optic nerves) had the highest amount of radiation dose spared with implementation of CODA. CODA can produce trajectories which inherently reduce radiation dose to non-target tissues on average, thus decreasing the likelihood of inducing non-target tissue complications during hypofractionated stereotactic radiosurgery.

Figure 9:
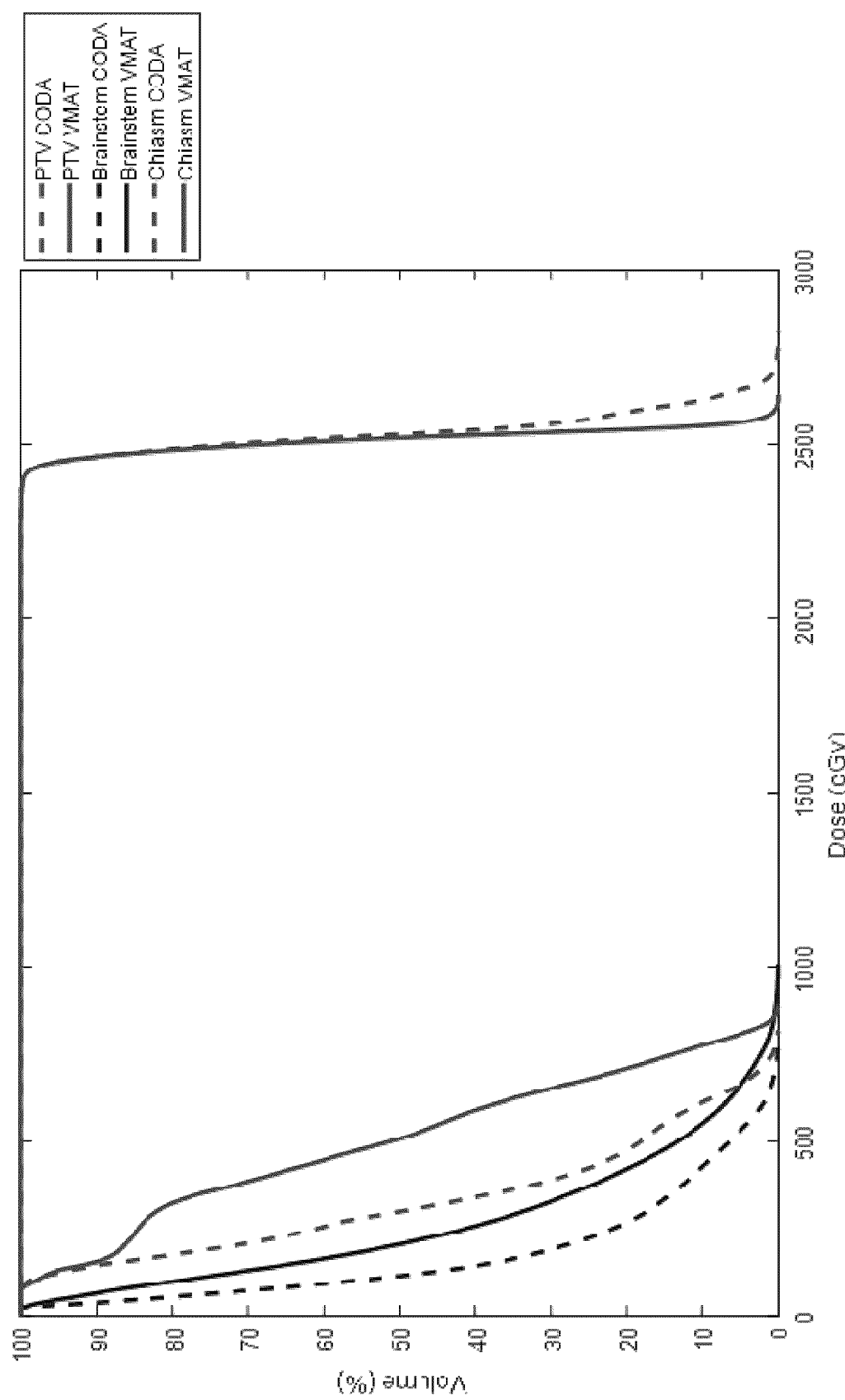
FIG. 9 shows a DVH comparison of the mean DVHs for the PTVs, brainstem, and chiasm (n=7). The dotted lines indicate the mean for CODA plans, while the solid lines indicate the mean for the VMAT plans.

FIG. 9 shows the mean dose-volume histograms (DVHs) over the test patient population for brainstem and chiasm (curves on the left side of the plot) and target volumes (curves on the right side of the plot), all treated to 24 Gy. This plot illustrates that while coverage was almost identical for both cases, there is sparing on the brainstem and chiasm DVHs across the population with implementation of CODA.

Figure 10:
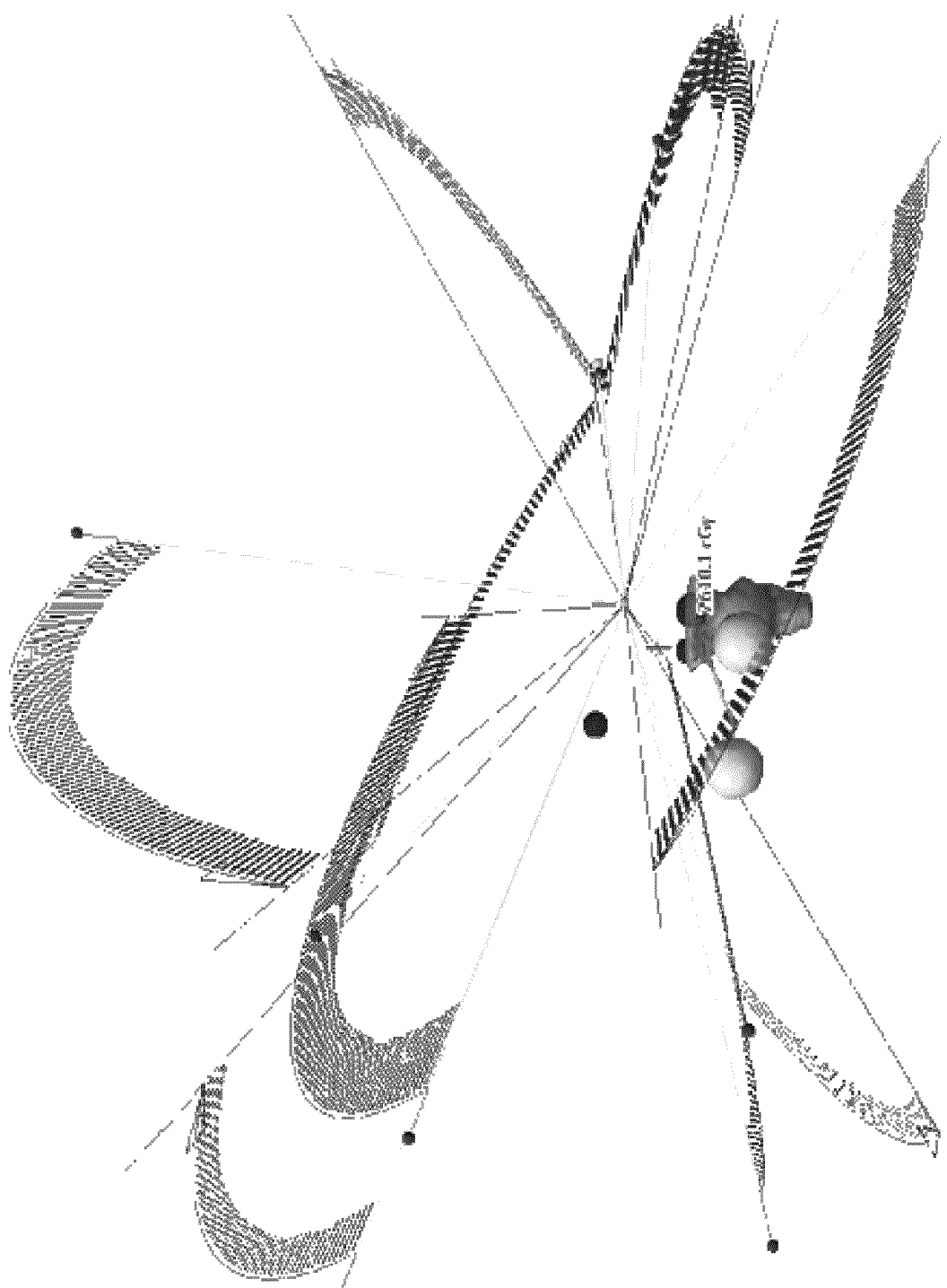
FIG. 10 shows an example of a CODA trajectory overlaid on patient anatomy.

FIG. 10 depicts the trajectory as planned via the CODA optimization for one of the three target cases in the study.

DISCUSSION

The very significant benefits from the disclosed automated trajectory optimization methods described herein are visible in FIGS. 7A to 9. In this test patient population, there was statistically significant sparing of radiation dose to the brainstem, which was the most proximal and most critical structure included in all treatment plans. This benefit was gained without compromise to target conformity, as both plans have almost identical average conformity values. FIG. 9 displays the agreement in target DVH and benefit to the average brainstem and chiasm DVHs with implementation of CODA. The radiation dose was normalized such that 24 Gy was assigned to cover 99.5% volume of the coldest target. At the shoulder of the average target DVHs, we can see excellent agreement between the results from the CODA and standard VMAT plans. While the maximum radiation dose in targets appears hotter on average for CODA than for standard VMAT, this difference is not statistically significant.

Figure 8A:
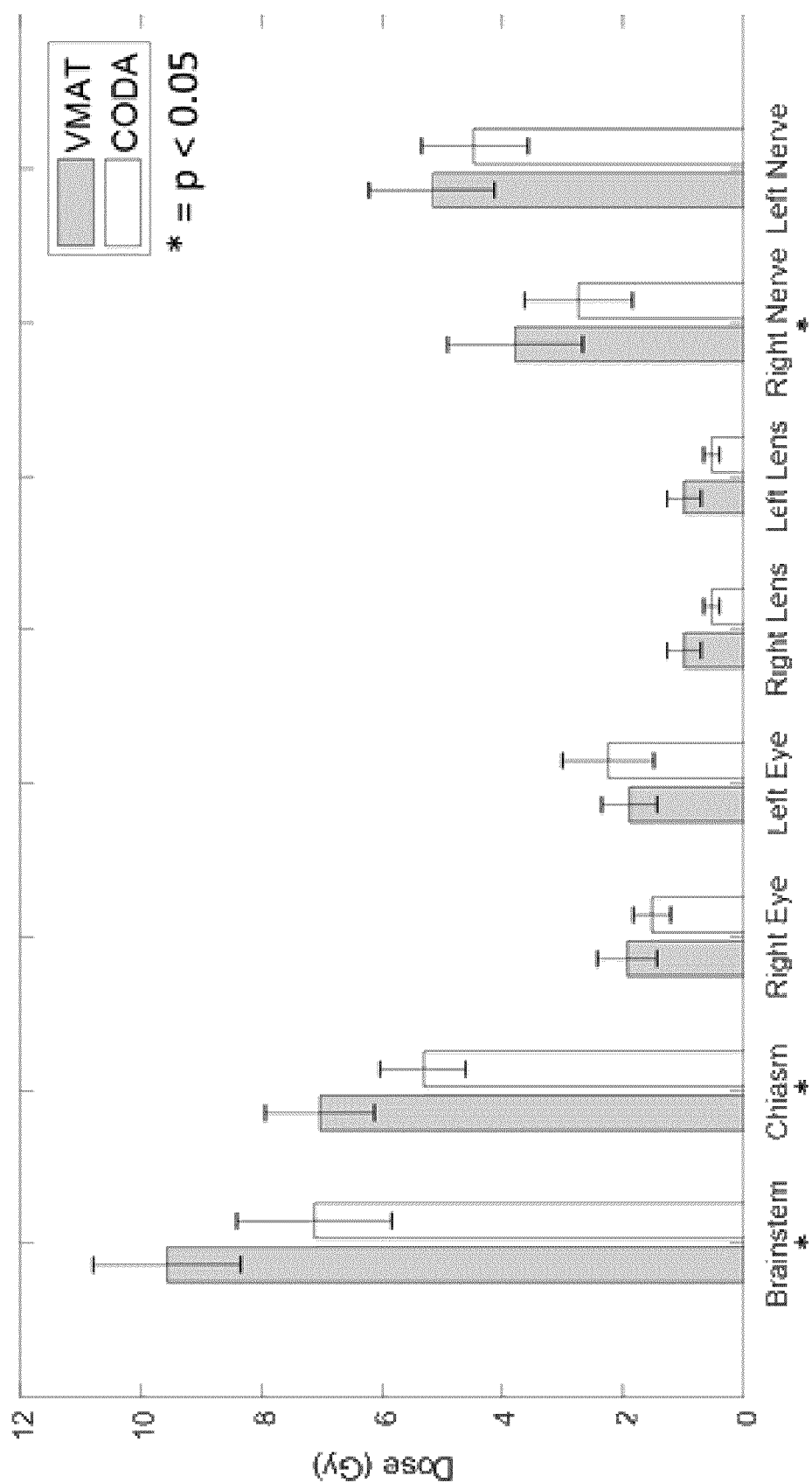
FIG. 8A shows a comparison of mean dose to OARs for OARs used in the optimization of CODA trajectories in the planning comparison (n=7). All error bars are standard error of the mean.

Additionally, FIG. 8 shows that this increased benefit to the brainstem did not come with a compromise of focus to any other OAR. On average, all OAR maximum radiation doses decreased with implementation of CODA, except for the left eye which increased by a statistically insignificant amount. FIG. 8A shows that the sparing of these OARs is not limited to the maximum radiation dose, but is present in mean radiation dose as well, indicating that sparing is occurring throughout the volume of the OAR with CODA when compared to standard VMAT. While mean radiation dose reduction could be of merit in the case of retreatment, in the context of single treatment maximum radiation dose is the clinically relevant metric.

Figure 7A:
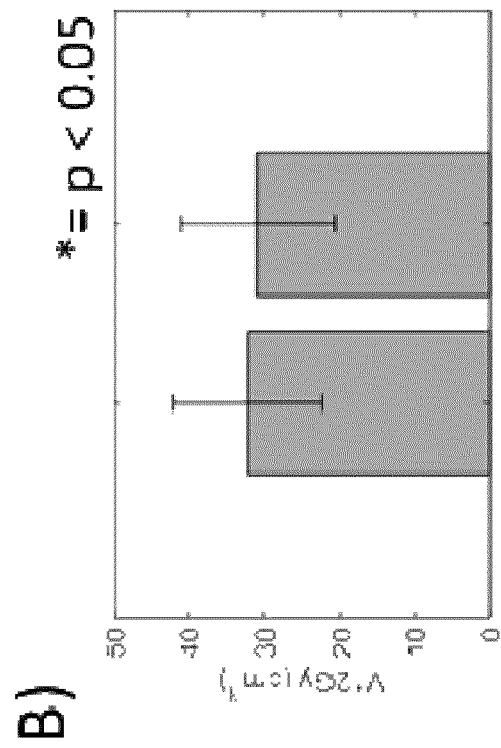
FIGS. 7A through 7D show planning metrics for a comparison of CODA and standard VMAT plans (n=7).
Figure 7B:
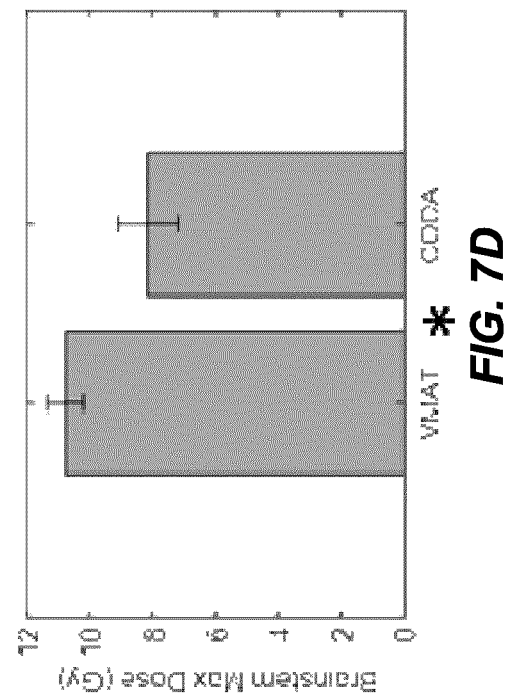
Figure 7C:
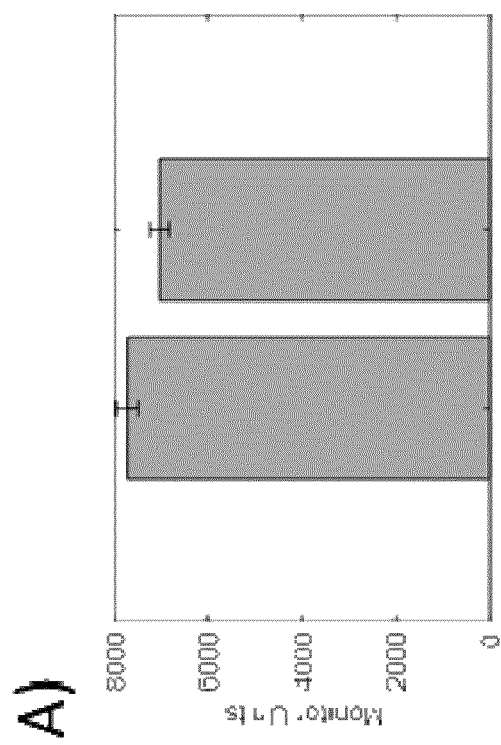
Figure 7D:
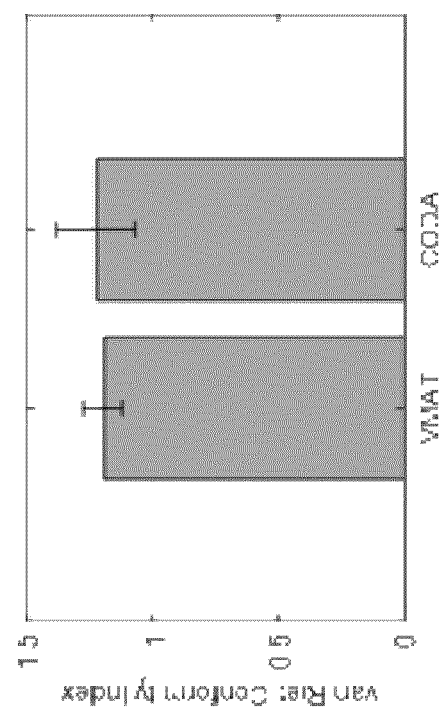

The redistribution of radiation dose to avoid OARs and retain target coverage has not increased the volume of brain receiving 12 Gy or higher. As indicated by FIG. 7B, there is a small, statistically insignificant reduction in the V12 Gy when compared to VMAT. FIG. 7A shows the improvement in MU efficiency with implementation of CODA. Six of the seven plans had fewer MU with implementation of CODA. The percent reduction in total MU for each of the cases was 6.65%, 12.9%, 7.43%, 10.2%, 17.7%, 16.7%, and −15.1%. The case which showed an increase in MU included the three targets closest to the brainstem, two of which were within 5 mm. This case required substantially more modulation to spare the brainstem than the other plans.

In the six plans showing decreased MU, the cause of this is likely two-fold: the decrease of the presence of OARs in the BEV leading to an increase in overall aperture area, and the optimization of the direction of MLC leaf travel via collimator optimization leading to an increase in the ability to deliver radiation dose to multiple targets simultaneously without irradiating the non-target tissue between them. A decrease in irradiation of non-target tissue will also result in less demand on the PRO algorithm, through NTO sparing, in order to reduce radiation dose to these tissues, which may result in less fluence modulation and fewer MU. This increased radiation dose efficiency leads to a decrease in the total required MUs, which may in turn decrease the total plan treatment time, hence reducing the opportunity for intrafraction motion to occur.

FIG. 10 is a visualization of trajectories produced from the CODA cube for a test patient in the dataset. The increase in the diverse number of planes of incident beams when compared to conventional trajectories is clear from this overlay on the patient anatomy. The selected trajectory visualized is overlaid on a test-patient anatomy. The noncoplanar nature of the selected arcs is visible as it achieves greater sampling of the $4\pi$ space compared to standard 4-arc VMAT planning.

While k-means clustering finds groups of candidate arcs which are spatially separated in the couch-gantry plane, there remains the possibility for these arcs to be very similar in their incident beam angle direction, leading to the potentially redundant inclusion of two arcs sampling the same space. Additionally, if this occurs on multiple arcs in the final arc solution, this could bias the radiation dose distribution toward this oversampled space. While this possibility was not found in this patient subset, and not detected in the clinical metrics examined, some embodiments may enforce separation of trajectories in the final trajectory set on the $4\pi$ sphere to promote efficient sampling.

While it is not guaranteed that the trajectory definition process returns the optimal set of arcs, the algorithm does enforce that the arcs are members of the optimal solution to their couch-gantry plane and are thus inherently (at least locally) low-cost, members of spatially separated clusters, and are long in gantry travel to promote flexibility in the optimizer. Additionally, an arc with a long gantry travel that is a member of an optimal low-cost solution for its couch-gantry plane is more likely to have a lower cost per control point than an arc with short gantry travel.

Gains will additionally be expected in trajectory optimization and dosimetric benefit with the removal of VMAT optimization restrictions in treatment planning systems, and the inclusion of simultaneous rotation of multiple LINAC axes.

Dynamic Trajectory CODA

These methods described herein may be generalized to trajectories with simultaneous movements in two degrees of freedom (e.g. simultaneous gantry rotation and couch rotation) by first navigating each couch-gantry plane using a minimum cost dynamic trajectory algorithm and finding the longest contiguous gantry-span regions in the three-dimensional space of the CODA cube from the candidate dynamic trajectories. In some embodiments the methods described herein are generalized to trajectories with simultaneous movements in three degrees of freedom (e.g. simultaneous gantry, couch and collimator rotation).

Another application of a CODA cube is to identify optimized dynamic trajectories using a gradient descent method. In some embodiments the gradient descent method searches for a path of lowest cost within an allowable range from every possible starting point in both directions of gantry travel. Using gradient descent in both directions of gantry travel can help to prevent gradient paths from becoming trapped in local maxima, or high-cost map convexities. A trajectory is navigable in either direction of gantry travel in delivery, but different candidate trajectories may be identified by gradient descent when the direction of navigation is changed.

To avoid trajectories which would violate mechanical restrictions preventing simultaneous rotation of the axes (dynamic couch and dynamic collimator) moving from gantry position to next gantry position, the gradient descent method may consider a finite number of next positions at every point in the trajectory. The algorithm identifies which of the available next positions are lowest cost. The algorithm selects this position as the next position in the trajectory.

FIGS. 11A and 11B schematically depict a 3D bi-direction gradient trajectory offering available next trajectory positions from a current position. FIG. 11A shows the available positions for cases where in-plane motion is not allowed. FIG. 11B shows the available next positions for cases where in-plane motion is permissible.

As FIG. 11B depicts, in-plane motion within the couch-collimator plane permits trajectories which have dynamic couch or collimator and fixed gantry. These in-plane motions may be allowed under specific geometric conditions to potentially improve the overall trajectory or increase the sampling of the 4π (or couch-gantry) space, which would be unattainable if in-plane motion is not allowed.

At a gantry position (e.g. in IEC 1612 coordinates) of 0 degrees and 180 degrees, the couch rotation offers no increased sampling of the 4π space, therefore in-plane motions may be restricted. However, at an angular gantry distance of at least n from 0 degrees and 180 degrees, in-plane motion produces couch arcs which increase sampling and may be allowable.

FIG. 12A shows a 3-dimensional plot of candidate (grey) trajectories and an optimal (black) trajectory. FIG. 12B shows the projection of all trajectories onto the couch-gantry plane. FIG. 12C shows the projection of all trajectories onto the collimator-gantry plane. In such embodiments, a mechanical restriction of A degrees of couch and collimator rotation per degree of gantry rotation may be imposed. For example, A may be 3 degrees in some embodiments.

Figure 13A:
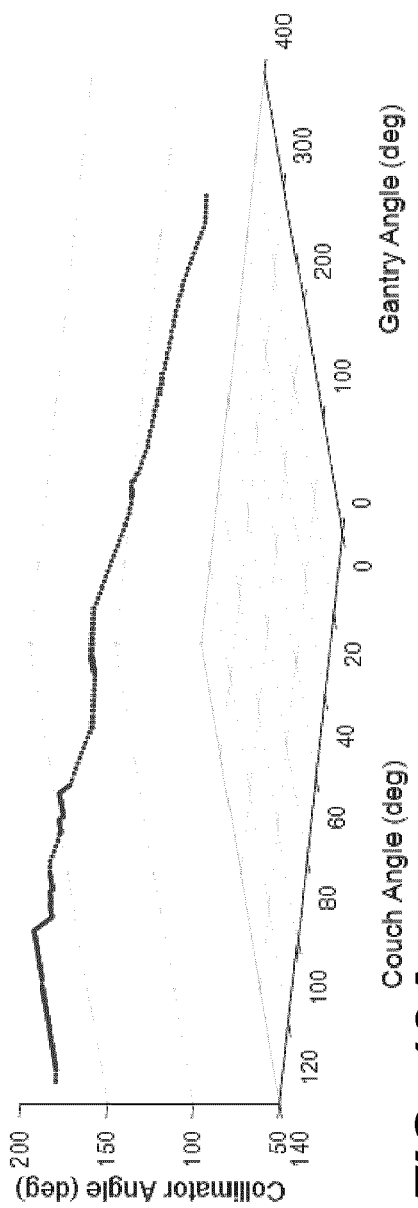
FIGS. 13A to 13C show a final low cost trajectory selected from the lowest cost trajectory produced from the bi-directional gradient search method with mechanical restriction of 1 degree of couch and collimator motion for every 1 degree of gantry motion.
Figure 13B:
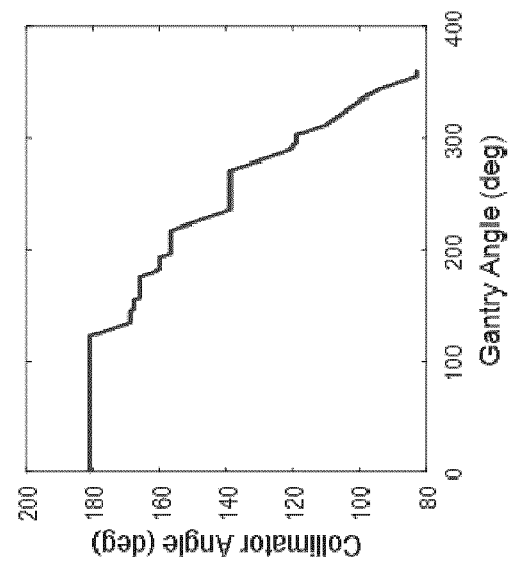
Figure 13C:
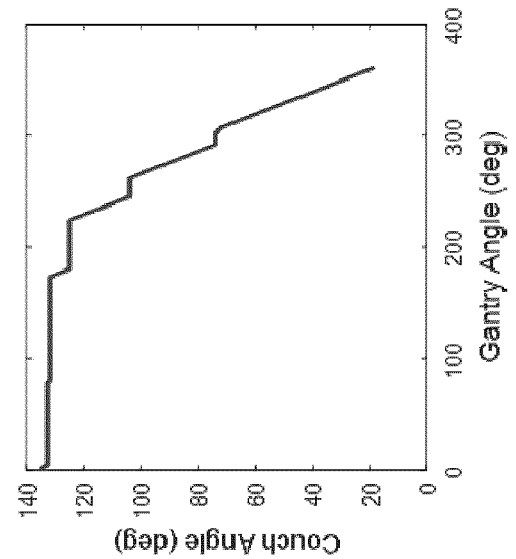

FIGS. 13A to 13C show final low cost trajectory selected from the lowest cost trajectory produced from the example bi-directional gradient search method with mechanical restriction of 1 degree of couch and collimator motion for every 1 degree of gantry motion. Searching is conducted from starting points sampled at every 5 degrees of couch and collimator to illustrate the method.

FIG. 13A is a 3-dimensional plot optimal trajectory. FIG. 13B is a projection of the trajectory onto the couch-gantry plane. FIG. 13C is the projection of the trajectory onto the collimator-gantry plane.

Example Radiation Dose Delivery System

Another aspect of the invention provides apparatus for radiation dose delivery. The apparatus may comprise a radiation dose delivery system or components for a radiation dose delivery system. One example radiation dose delivery system is illustrated in FIG. 14.

Figure 14:
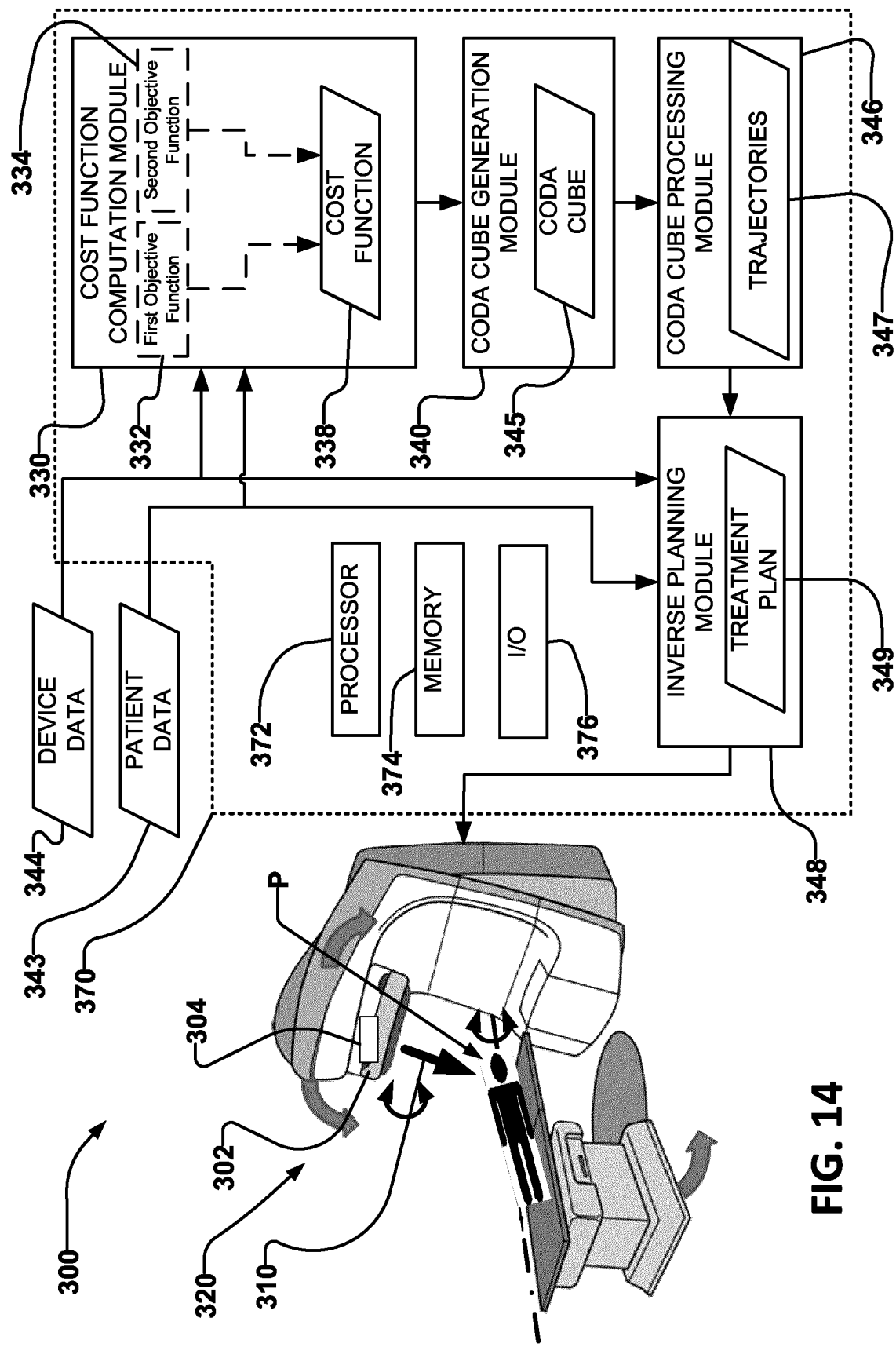
FIG. 14 shows an example radiation dose delivery (radiotherapy) system.

FIG. 14 shows example radiation dose delivery system 300. System 300 includes a radiotherapy device 320. Device 320 comprises a radiation source 304 supported on a gantry 302. Radiation source 304 may, for example, comprise a linear accelerator. Radiation source 304 may be controllable to emit a radiation beam 310 toward a patient P. Device 320 may include motors or the like connected to move radiation source 304 relative to patient P. In the illustrated embodiment gantry 302 may be rotated, thereby rotating the point of origin of radiation beam 310 in an arc around patient P.

Device 320 may take different forms which provide for motion of radiation source 304 relative to a patient P. For example, device 320 may comprise a linear accelerator or other radiation source having a rotatable gantry (like radiotherapy device 100 described herein) or a robotic radiosurgery system such as the Cyberknife™ system. Different types of device 320 may provide different mechanisms for shaping radiation beam 310.

System 300 may also include a data processing system such as computer 370. Computer 370 comprises one or more processors 372, memory 374 and I/O (i.e. input/output) interface 376. I/O interface 376 may comprise one or more output devices which permit data to be output from computer 370 to a user (not shown) such as, for example, one or more displays, a printer or the like. I/O interface 376 may also comprise one or more input devices which permit the user to provide data to computer 370 such as, for example, a mouse, a keyboard, a touch-screen or the like. In some embodiments, I/O interface 376 comprises a network interface for communicating data to and/or from computer 370 via a suitable network.

In some embodiments, computer 370 is configured to generate a radiation treatment plan 349 to be used by radiotherapy device 320 to deliver a course of radiation treatment. Plan 349 may include instructions which may be executed by a control system of device 320. In some embodiments, computer 370 is configured to control one or more parameters of radiotherapy device 320 during a course of radiation treatment. Such parameters may, for example, include trajectories of radiation beam 310, radiation dose, collimator leaf settings, fluence, beam energy or the like. In some embodiments plan 349 defines a series of control points.

A data processor such as computer 370 may, for example, comprise a cost function computation module 330, a CODA cube generation module 340, a CODA cube processing module 346 and an inverse planning module 348.

Cost function computation module 330 processes patient data 343 together with device data 344 and generates cost function values 338 which correspond to possible physical configurations of device 320.

Patient data 343 may, for example, be like patient data 43 described herein. Patient data 343 specifies bounds of one or more target volumes and optionally specifies bounds of one or more OARs and/or outer bounds of patient P. In some embodiments, patient data 343 may be obtained from memory 374. In some embodiments, patient data 343 may be provided in real-time using I/O interface 376.

Device data 344 relates to the capabilities of a radiotherapy device (e.g. device 320). The device data may include, for example one or more of:
  a model of a MLC or other beam shaper provided by the device 320;
  information regarding the degrees of freedom provided by the device 320 for motion of radiation source 304;
  information regarding configurations of device 320 that could cause collisions (e.g. between gantry 301 and a couch);
  information regarding the capabilities of device 320 such as whether or not different degrees of freedom can be simultaneously controlled, how quickly configuration of the device 320 can be changed relative to different axes or other degrees of freedom;
  etc.

In some embodiments, cost function 338 optionally comprises a plurality of objective functions that are combined to yield cost function values 338. FIG. 14 shows first objective function 332 and second objective function 334.

In some embodiments, first and second objective functions 332, 334 include an objective function that provides a measure of how well beam 310 may be shaped to fit one or more PTVs for a configuration of device 320 (a whitespace measure is an example of this). In some embodiments, first and second objective functions 332, 334 include an objective function that provides a measure of how much radiation dose would be provided to OARs for a configuration of device 320 (a 4π objective function as described herein is an example of this). Objective functions 332, 334 may, for example, be as described elsewhere herein.

CODA cube generation module 340 stores cost function values 338 in a data structure to provide CODA cube 345. CODA cube 345 may, for example, be stored in memory 374.

CODA cube processing module 346 processes CODA cube 345 generating a set of trajectories 347 to be used by radiotherapy device 320 during a course of radiation treatment. Trajectories 347 may be generated using CODA cube 345 in the manner described herein for trajectories 47, for example.

Inverse planning module 348 uses trajectories 347 together with patient data 343 and device data 344 to generate a treatment plan 349. Radiation treatment plan 349 may comprise instructions and/or data used by radiotherapy device 320 to deliver a course of radiation treatment.

In some embodiments, radiation treatment plan 349 is recorded in memory 374. In some embodiments, radiation treatment plan 349 is output to a user using I/O interface 376. In some embodiments, radiation treatment plan 349 may be distributed using a network interface.

In some embodiments, one or more data processors included in system 300 are configured to perform any of the methods described herein. For example, computer 370 may be configured to perform method 40 described herein.

The present technology may be applied to provide automated optimization of multiple-axes trajectory of a radiation treatment plan. Such optimization can yield radiation treatment plans which significantly reduce the number of total MU and/or significantly spare radiation doses to critical surrounding OARs without compromising the radiation dose to the target. Embodiments of the technology may be provided in the form of a complete trajectory generation system which requires no user intervention to produce trajectories which may yield improved delivery of radiation. Such a system may be stand-alone or integrated with other systems. Embodiments of the technology may provide methods for automatically detecting geometric challenges of demanding multiple metastasis plans and suggesting optimal arc arrangements.

The present technology may be configured as described herein to take into account possible limitations of radiotherapy devices and/or treatment planning systems and is immediately implementable clinically.

In some embodiments the systems and/or methods described herein are applied to intensity-modulated radiation therapy (IMRT). In some embodiments the system and/or methods described herein are applied to fixed port IMRT. In some embodiments the systems and/or methods described herein are applied to non-coplanar IMRT.

Interpretation of Terms

Unless the context clearly requires otherwise, throughout the description and the claims:
- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.
- "isocentre" means a point in space about which the gantry, couch and/or collimator rotate. For example a rotation axis of a couch and a rotation axis of a gantry may intersect at the isocentre of a radiation delivery device such as a linear accelerator. Alternatively, or in addition, the isocentre may be a point through which the radiation beam's central rays pass.
- "Control point": a point in a treatment delivery at which mechanical and/or radiation parameters are defined (e.g. MLC leaf positions, gantry angle, couch angle, collimator angle, beam energy, dose rate, etc.). When a treatment delivery is defined by a series of control points, the treatment delivery system may implement a form of interpolation (e.g. linear interpolation) to determine the values of some or all of these parameters at points between the control points.
- "Trajectory" means a path along which a radiation source can be moved relative to a patient. A trajectory may involve motions in one or more degrees of freedom. A trajectory may, for example, comprise changes in one or more of a couch angle and a gantry angle in a radiotherapy device of the general type illustrated in FIG. 1.
- "Arc" is a trajectory in which a radiation source moves in an arc relative to the patient. For the type of radiotherapy device shown in FIG. 1 at least one of the couch and gantry is in motion while the radiation beam is on to generate an arc. Some arcs may involve motion of only one degree of freedom. For example, an arc may be provided by rotating a gantry while the couch does not move. Such "static couch arcs" are a limiting case of a more general definition of an arc. An arc may be specified by a discrete set of control points that can be sequentially delivered by the treatment delivery system without needing to turn off the beam between control points.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

Where processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

One or more aspects of the invention may also be provided in the form of a program product. The program product may comprise any non-transitory medium which carries a set of computer-readable instructions which, when executed by a data processor, cause the data processor to execute a method of the invention. For example, the instructions may cause the processor to generate a set of CODA trajectories and/or a treatment plan using CODA trajectories as described herein. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Aspects of the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Various features are described herein as being present in "some embodiments". Such features are not mandatory and may not be present in all embodiments. Embodiments of the invention may include zero, any one or any combination of two or more of such features. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method for controlling radiation delivery by a radiotherapy device having plural degrees of freedom of motion of a radiation source relative to a patient, the method comprising:
   generating a data structure representing a cost space having three or more dimensions by:
      computing a value of a cost function based on patient data and machine data for each of a plurality of coordinate points wherein each of the coordinate points corresponds to a set of control point values, each of the sets of control point values comprising, for each of the plural degrees of freedom, a position of the radiotherapy device in the corresponding degree of freedom; and
      storing the resulting values of the cost function in locations in a data store associated with the corresponding coordinate points;
   processing the data in the data structure to determine plural candidate trajectories of the radiotherapy device that each pass successively through neighboring ones of the coordinate points and for which a sum of the cost function values over the candidate trajectory is smaller than for other possible trajectories;
   generating a radiation delivery plan using a treatment plurality of the candidate trajectories, the treatment plurality of the candidate trajectories comprising a treatment set of the coordinate points corresponding to the treatment plurality of candidate trajectories and the sets of control point values corresponding to the treatment set of the coordinate points;

communicating the radiation delivery plan to a radiotherapy device; and delivering radiation to the patient by the radiotherapy device according to the radiation delivery plan, wherein delivering radiation comprises moving the radiotherapy device, in the plural degrees of freedom, through the positions associated with the sets of the control point values corresponding to the treatment set of coordinate points to thereby irradiate the patient with radiation from the radiation source.

2. The method according to claim 1 comprising selecting the plurality of the candidate trajectories using a clustering algorithm.

3. The method according to claim 2 wherein the clustering algorithm comprises a k-means clustering algorithm.

4. The method according to claim 2 wherein selecting the plurality of the candidate trajectories comprises selecting the longest candidate trajectory from each of a plurality of clusters determined by the clustering algorithm.

5. The method according to claim 1 wherein the plural degrees of freedom include a gantry angle, a couch angle and a collimator rotation angle.

6. The method according to claim 5 wherein the candidate trajectories lie in planes in which one direction in the planes corresponds to gantry angle and another direction in the planes corresponds to couch angle.

7. The method according to claim 6 comprising separately identifying candidate trajectories in each of plural ones of the planes.

8. The method according to claim 7 comprising, for each of the planes finding a set of not more than $N_{max}$ candidate trajectories that piecewise span the full range of possible gantry angles with a minimum total cost.

9. The method according to claim 8 further comprising constraining the candidate trajectories to satisfy a trajectory length criterion requiring each candidate trajectory to have at least a minimum length.

10. The method according to claim 5 wherein each of the candidate trajectories comprises an arc along which gantry angle changes and couch angle is fixed.

11. The method according to claim 1 wherein processing the data in the data structure to determine the candidate trajectories comprises applying a Bellman-Ford algorithm.

12. The method according to claim 1 wherein generating the radiation treatment plan comprises performing inverse optimization.

13. The method according to claim 12 wherein the radiotherapy device comprises a multi-leaf collimator and the inverse optimization adjusts collimator leaf configuration for the multi-leaf collimator along the treatment trajectories.

14. The method according to claim 12 wherein the inverse optimization comprises adjusting radiation dose rate along the treatment trajectories.

15. The method according to claim 1 wherein the candidate trajectories involve motions in one of the degrees of freedom only.

16. The method according to claim 1 wherein the cost function comprises plural objective functions.

17. The method according to claim 16 comprising determining a mean of the values of the plural objective functions.

18. The method according to claim 17 wherein the objective functions comprise a $4\pi$ objective function and a whitespace objective function.

19. The method according to claim 1 wherein the cost function increases cost based on dose delivered to organs at risk (OARs) identified in the patient data.

20. The method according to claim 1 wherein the cost function increases cost based on dose delivered to non-target tissues.

21. The method according to claim 1 wherein the data structure comprises a cube having dimensions that span the entire range of the degrees of freedom.

* * * * *